United States Patent [19]
Reynolds

[11] Patent Number: 6,008,013
[45] Date of Patent: Dec. 28, 1999

[54] CHONDROCYTE PROTEINS

[75] Inventor: Paul R. Reynolds, Rochester, N.Y.

[73] Assignee: University of Rochester, Rochester, N.Y.

[21] Appl. No.: 08/680,506

[22] Filed: Jul. 8, 1996

Related U.S. Application Data

[60] Provisional application No. 60/021,672, Jul. 5, 1996.
[51] Int. Cl.$^6$ ................. C12P 21/00; C07H 21/04; C07K 14/46
[52] U.S. Cl. ............ 435/69.1; 435/252.3; 536/23.5; 935/23; 530/350
[58] Field of Search .................. 435/69.1, 240.2, 435/252.3; 536/23.5; 935/23; 530/350

[56] References Cited

U.S. PATENT DOCUMENTS

| | | | |
|---|---|---|---|
| 5,106,748 | 4/1992 | Wozney et al. | 435/252.3 |
| 5,250,302 | 10/1993 | Oppermann et al. | 424/422 |
| 5,266,683 | 11/1993 | Oppermann et al. | 530/326 |
| 5,270,303 | 12/1993 | Suzuki et al. | 514/21 |
| 5,324,819 | 6/1994 | Oppermann et al. | 530/350 |
| 5,366,875 | 11/1994 | Wozney et al. | 435/69.1 |
| 5,368,858 | 11/1994 | Hunziker | 424/423 |
| 5,444,157 | 8/1995 | Suzuki et al. | 530/395 |
| 5,453,419 | 9/1995 | Murakami et al. | 514/12 |
| 5,459,047 | 10/1995 | Wozney et al. | 435/69.1 |
| 5,468,845 | 11/1995 | Oppermann et al. | 530/387.9 |

FOREIGN PATENT DOCUMENTS

| | | |
|---|---|---|
| 0635518 A1 | of 0000 | European Pat. Off. . |
| 931908 | 9/1993 | WIPO . |

OTHER PUBLICATIONS

Sambrook et al. Molecular Cloning: A Laboratory Manual Second Edition vols. 1, 2 and 3. Cold Spring Harbor Laboratory Press: Cold Spring Harbor, New York, U.S.A. Nov., 1989.

Bowie et al. Deciphering the message in protein sequences: tolerance to amino acid substitutions. Science, (Mar. 16, 1990) 247 (4948) 1306–10.

Meinkoth et al. Hybridization of nucleic acids immobilized on solid supports. Anal Biochem May 1984 1;138(2):267–284.

Capasso et al., "The culture of chick embryo chondrocytes and the control of their differentiated functions in vitro," *Experimental Cell Research*, 142:197–206 (1982).

Ryan et al., "Differential expression of a cysteine–rich domain in the amino–terminal propeptide of type II (cartilage) procollagen by alternative splicing of mRNA," *The Journal of Biological Chemistry*, 265:10334–10339 (1990).

Yang et al., "Human ceruloplasmin," *Journal of Biological Chemistry*, 265:10780–10785 (1990).

Ikeda et al., "In situ hybridization of bone matrix proteins in undecalcified adult rat bone sections," *Journal of Histochemistry and Cytochemistry*, 40:1079–1088 (1992).

Bang et al., "Isolation and characterization of a cartilage–specific membrane antigen (CH65): comparison with cytokeratins and heat–shock proteins," *Immunology*, 81:322–329 (1994).

Houston et al., "Molecular cloning and expression of bone morphongenetic protein–7 in the chick epiphyseal growth plate," *Journal of Molecular Endocrinology*, 13:289–301 (1994).

Nah et al., "An alternative transcript of the chick type III collagen gene that does not encode type III collagen," *Journal of Biological Chemistry*, 269:16443–16448 (1994).

Chen et al., "Progression and recapitulation of the chondrocyte differentiation program: cartilage matrix protein is a marker for cartilage maturation," *Developmental Biology*, 172:293–306 (1995).

Koyama et al., "Syndecan–3, tenascin–c, and the development of cartilaginous skeletal elements and joints in chick limbs," *Developmental Dynamics*, 203:152–162 (1995).

Stoilov et al., "A common FGFR3 gene mutation is present in achondroplasia but not in hypochondroplasia," *American Journal of Medical Genetics*, 55:127–133 (1995).

Tsumaki et al., "Differential expression of an acidic domain in the amino–terminal propeptide of mouse pro–α2(XI) collagen by complex alternative splicing," *The Journal of Biological Chemistry*, 270:2372–2378 (1995).

Healy et al., "Expression of the chicken Sox9 gene marks the onset of the cartilage differentiation," *Abstracts from the New York Academy of Sciences Mtg. on Molecular and Developmental Biology of Cartilage* (Sep. 27–30, 1995).

Hillarby et al., "Localisation of novel gene expression in bovine growth plate," *Abstracts from the New York Academy of Sciences Mtg. on Molecular and Developmental Biology of Cartilage* (Sep. 27–30, 1995).

Nurminskaya et al., "Analysis of up–regulated genes during chondrocyte hypertrophy," *Abstracts from the New York Academy of Sciences Mtg. on Molecular and Developmental Biology of Cartilage* (Sep. 27–30, 1995).

Reynolds et al., "Alternative splicing of a chondrocyte–specific gene," *Abstracts of the MDBC Mtg*, (Bethesda, MD) (Sep. 1995).

Reynolds et al., "Alternative splicing of a chondrocyte–specific gene," *Abstracts of the 1995 Am. Soc. Bone. Miner. Res. Mtg.* (Baltimore, MD) (Sep. 1995).

*Primary Examiner*—Elizabeth Kemmerer
*Assistant Examiner*—David S. Romeo
*Attorney, Agent, or Firm*—Nixon Peabody LLP

[57] ABSTRACT

The present invention relates to an isolated protein or polypeptide selectively expressed in chondrocytes in lower proliferative or upper hypertrophic zones of long bone and embryonic vertebrae growth plates as well as to antibodies, fragments, and probes recognizing these proteins or polypeptides. The proteins or polypeptides can be used for treating non-union bone defects. The antibodies, binding portions thereof, and probes can be used to inhibit arthritic progression of articular chondrocytes. The antibodies, binding portions thereof, and probes can also be used to identify the occurrence of chondrocytes proliferation or hypertrophy. The encoding DNA molecule, either alone in isolated form or in an expression system or a host cell, is also disclosed.

17 Claims, 8 Drawing Sheets

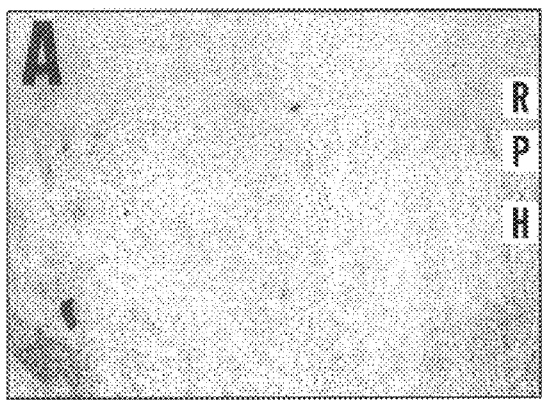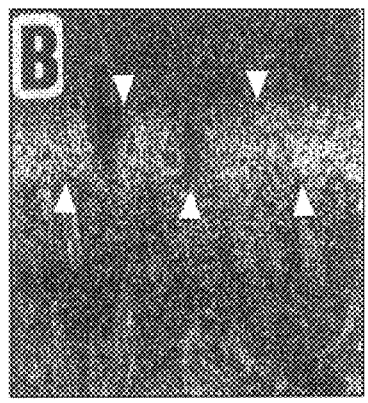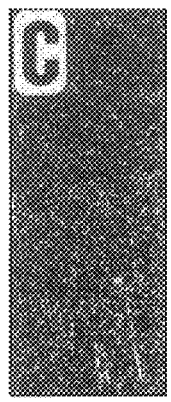
FIG. 2A   FIG. 2B   FIG. 2C
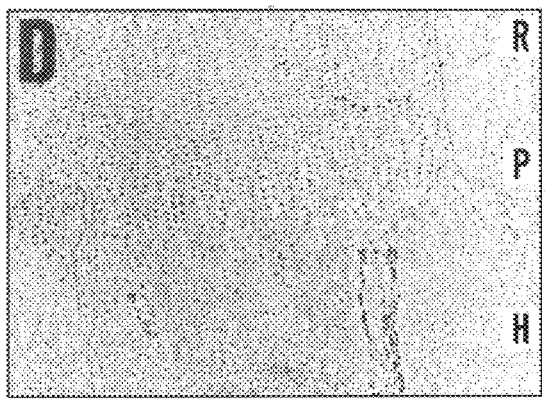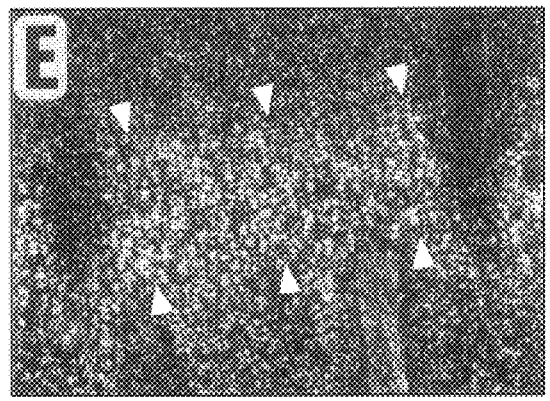
FIG. 2D   FIG. 2E
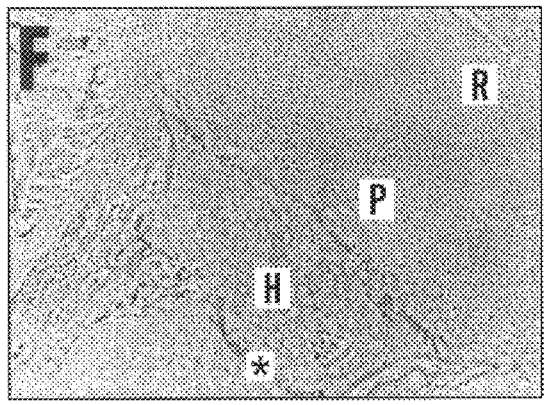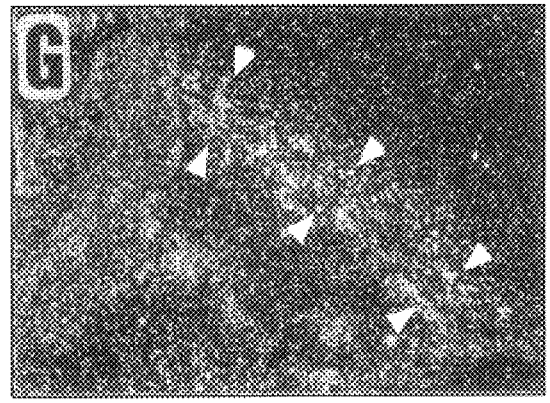
FIG. 2F   FIG. 2G

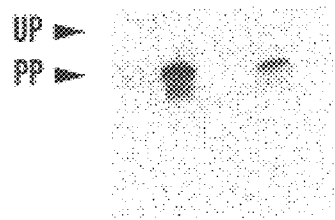

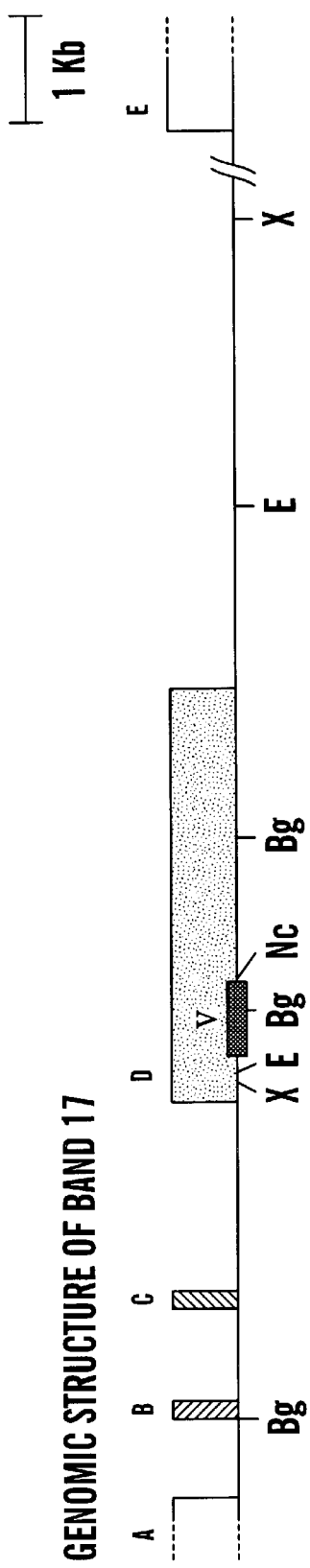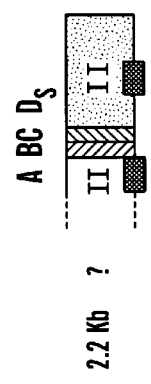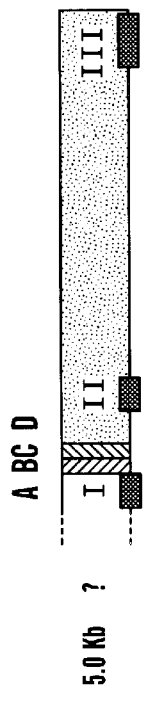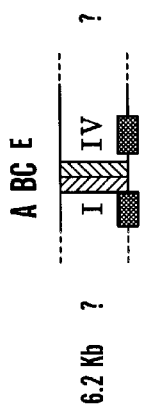
FIG. 5A
FIG. 5B

FIG. 7

```
  1  CGCCGCGACATGGAAACACCTGGGCGCGGCCGCCTGGCCGCCCGCCGCTCCCCCGGCCGCTCTTCGCC
     R  R  D  M  E  H  L  A  R  R  L  A  A  R  F  P  A  L  F  A
                                                 Pst I
 61  GCCCGCCGCGCGCCTGGCGCTGGCCAGCAGCTCCAAGCACCGCTGCCTGCAGAGCGGCGCG
     A  R  R  R  L  A  L  A  S  S  S  K  H  R  C  L  Q  S  G  A
121  GCCTTCCGGCGCGGCCTCGGGCCCTCCAGCCTCGGCGCCCTGGCGGCGGAGACGGAGATCGAA
     A  F  R  R  G  L  G  P  S  L  S  L  G  A  D  E  T  E  I  E
181  GTGAACGACGCGCTGATGAGGTTTTTTGATCACTGCGACAAGTTCGTGGCCTTCGTGGAG
     V  N  D  A  L  M  R  F  F  D  H  C  D  K  F  V  A  F  V  E
241  GACAACGACACAGCCATGTACCAAGTGAACGCCTTCAAAGAGGGCCCGGAGATGAGGAAG
     D  N  D  T  A  M  Y  Q  V  N  A  F  K  E  G  P  E  M  R  K
                                                   A  B Bgl II
301  GTGTTGGAGAAGGTGGCGAGTGCCCTGTGTCTGCCCGCGCAGGAGCTGAACGCCAG ATCTC
     V  L  E  K  V  A  S  A  L  C  L  P  A  S  E  L  N  A  D  L
361  GTTCAAGTGGCTTCCTCACTTGCTCGTATGAGTTGGCTATAAAAATGTGACCTCCCG
     V  Q  V  A  F  L  T  C  S  Y  E  L  A  I  K  N  V  T  S  P
                       B  C
421  TGGTGTTCGCTCTTCAGTGAAGAAGATGCTAAG GTACTGGAGTACCTGAATGACCTGAAG
     W  C  S  L  F  S  E  E  D  A  K  V  L  E  Y  L  N  D  L  K
481  CAATACTGGAAGAGAGGATATGGCTATGACATCAATAGTCGCTCCAGCTGCATTTTATTC
     Q  Y  W  K  R  G  Y  G  Y  D  I  N  S  R  S  S  C  I  L  F
                                                         C  E
541  CAGGATATCTTCCAGCAGTTGGACAAAGCAGTGGATGAGAGCAGAAG TTCAAAACCCATT
     Q  D  I  F  Q  Q  L  D  K  A  V  D  E  S  R  S  S  K  P  I
                                             Xmn I
601  TCTTCACCTTTGATTGTACAAGTTGGACATGCAGAAACACTTCAGCAGCCACTTCTTGCTCTT
     S  S  P  L  I  V  Q  V  G  H  A  E  T  L  Q  Q  P  L  L  A  L

661  ATGGGCTACTTCAAAGATGTGAGCCTCTCCAGGCCAACAATTACATCCGCCAGGCGCAT
     M  G  Y  F  K  D  A  E  P  L  Q  A  N  N  Y  I  R  Q  A  H
721  CGGAAGTTCCGCAGCGGCCGGATAGTGCCTTATGCCTTATCAGCGCAACCTGGTCTTTGTGCTGTAC
     R  K  F  R  S  G  R  I  V  P  Y  A  A  N  L  V  F  V  L  Y
781  CACTGTGAGCAGAAGACCTCTAAGGAGGAGTACCAAGTGCAGATGTTGCTGAATGAAAAG
     H  C  E  Q  K  T  S  K  E  E  Y  Q  V  Q  M  L  L  N  E  K
841  CCAATGCTCTTTCATCACTGCAATGAAAACCATCTCCAGTTATGCAGACCTCAAGAGCTAT
     P  M  L  F  H  H  S  N  E  T  I  S  T  Y  A  D  L  K  S  Y
901  TACAAGGACATCCTTCAAAACTGTCACTTCGAAGAAGTGTGTGAATTGCCCAAAGTCAAT
     Y  K  D  I  L  Q  N  C  H  F  E  E  V  C  E  L  P  K  V  N
         Kpn I
961  GGTACCGGTTGCTGACGAACTTTGAGGGAATGAAATGGAGTGGCCGATTTGGAAACCGATC
     G  T  V  A  D  E  L  *
991  TCAGTTTTCTTCAACAGATGTTGTGAACGAGCACTTTGGATGCAATGCTGCTGTGTGCC
```

NUCLEOTIDE HOMOLOGY (PERCENT IDENTITY: 67.937)

```
193 CTGATGAGGTTTTTGATCACTGCGACAAGTTCGTGGCCTTCGTGGAGGACAACGACACAGCCATGTACC
      |||||||||||| ||||||||: ||||||   |||||||||||||    ||| |||||||
  8 CTAATGAGATTTTTGATCACTGTGAGANGTTTTTAACTGAAGTAGAAAAAATGCTACAGCTCTTTATC

263 AAGTGAACGCCTTCAAAGAGGGCCCGGAGATGAGGAAGGTGTTGGAGAAGGTGGCCGAGTGCCCTGTCT
     |||||| |||||||||||  ||||| |||||||||||| ||   |||||||   ||  ||||  |
 78 ACGTGGAAGCCTTCAAAACTGGACCAGAAATGCAGAACATTTTAAAAAAGTTGCAGCTACTTTGCAAGT

333 GCCGGCCAGCGAGCTGAAACGCAGATCTCGTTCAAGTGCCTTCCTCACTTGCTCGTCGTATGAGTTGGCTATA
      || |||||| |||||||   ||| | ||| || | |||  ||||||   |||  || || || || |||
148 GCCAGTAAATGATTTAAATGCAGATTTAATTCAAGTAGCCTTTTCACCTGTTCATTTGACCTGGCAATT

403 AAAAATGTGACCTCCCCGTGGTGTTCGCTCTTCAGTGAAGAAGATGCTAAGGTACTGGAGTACCTGAATG
    |||| |||   ||| ||| ||||||| | |||  ||  || || |||| |||  ||| || || ||||
218 AAAGGTGTTAAATCTCCTTGGTGTGATGTTTTGACATAGATGATGCAAAGGTATTAGAATATTTAAATG

473 ACCTGAAGCAATACTGGAAGAGAGGATATGGCTATGACATCAATAGTCGCTCCAGCTGCATTTTATTCCA
    | ||||| |||ACAATATTGGAAAAGAGGATATGGTATACTATTAACAGTCGATCCAGCTGCACCTGTTTCA
288 ATCTGAAACAATATTGGAAAAGAGGATATGGTATACTATTAACAGTCGATCCAGCTGCACCTGTTTCA

543 GGATATCTTCCAGCAGTTGGACAAAGCAGTGGATGAGAGCAGAAGTTCAAAACCCATTCTTCACCTTTG
    ||||||||||||||  ||||||| ||||||| ||| | |||||| |||| || |||||||||| ||
358 GGATATCTTCAGCACTTGGACAAAGCAGTTGAACAGAAAACAAAGGTCTCAGCCAATTTCTTCTCCAGTC

613 ATTGTACAAGTTGGACACATGCAGAAAC       638
    ||   |||||||| |||||||||||| |
428 ATCCTCCAGTTTGGTCATGCAGAGAC         453
```

FIG. 8A

AMINO ACID HOMOLOGY (PERCENT IDENTITY: 69.536)

```
 63 DALMRFFDHCDKFVAFVEDNDTAMYQVNAFKEGPEMRKVLEKVASALCLPASELNADLVQVAFLTCSYEL
    |||||||||||:|||||:||::|:||:|||||||||||||||:|||:|||||||||||||||||:|
  1 DKLMRFFDHCEXFLTEVEKNATALYHVEAFKTGPEMQNILKKVAATLQVPVNDLNADLIQVAFFTCSFDL

133 AIKNVTSPWCSLFSEEDAKVLEYLNDLKQYWKRGYGYDINSRSSCILFQDIFQQLDKAVDESRSSKPISS
    ||:||:|||||:|||:||||||||||||||||||||:|||||||:|||||||:|||||||:|:||||
 71 AIKGVKSPWCDVFDIDDAKVLEYLNDLKQYWKRGYGYTINSRSSCTLFQDIFQHLDKAVEQKQRSQPISS

203 PLIVQVGHAET   213
    |||:|.|||||
141 PVILQFGHAET   151
```

FIG. 8B

CHONDROCYTE PROTEINS

This application claims the benefit of U.S. Provisional Patent application Ser. No. 60/021,672, filed Jul. 5, 1996.

This work was supported by the National Institutes of Health Grant No. AR38945. The Federal Government may have certain rights in the invention.

FIELD OF THE INVENTION

The present invention relates to proteins expressed in chondrocytes, DNA molecules encoding these proteins, and their uses.

BACKGROUND OF THE INVENTION

Endochondral ossification is remarkably similar in diverse biological settings. The remodeling of calcified cartilage into bone can be found in embryonic sterna, vertebrae, and limbs, juvenile long bone development, fracture healing by callus formation, and ectopic bone formation induced by bone morphogenetic proteins. The same process can also be found in pathologic conditions, such as cartilaginous neoplasms, heterotopic ossification, and degenerating articular cartilage. This commonality suggests that mineralizing chondrocytes are committed to the same innate developmental pathway.

During the process of endochondral ossification, chondrocytes undergo a progression of maturational changes, with marked biochemical and physical changes in both the cells and surrounding matrix. These changes are most evident in the growth plate where they are spatially and temporally ordered (Buckwalter et al., *J. Bone and Joint Surg.*, 68A:243–255 (1986); Gibson et al., *Cell Biol.*, 101:277–284 (1985); and Poole, "Cartilage in Health and Disease", *Arthritis and Allied Conditions: A Textbook of Rheumatology*, 279–333, (1993)). Resting chondrocytes are flat, irregularly-shaped nondividing cells. As these cells enter the cell cycle, they become arranged in columns and undergo the rapid proliferation necessary for long bone growth. Collagen fibrils in the resting and proliferating region of the growth plate are predominantly type II collagen with associated minor collagens type IX and type XI (Buckwalter *Clin. Orthop.*, 172:207–231 (1983) ("Buckwalter"); Oshima et al., *Calcif. Tiss. Int.*, 45:182–192 (1989) ("Oshima"); Castagnola et al., *J. Cell Biol.*, 102:2310–2317 (1986); Liu et al., *Dev. Dynamics*, 198:150–157 (1993); and Linsenmyer et al., *Development*, 111, 191–196 (1991)). The matrix is characterized by an abundance of high molecular weight proteoglycans, which have a structural role in addition to preventing calcification (Buckwalter; Dziewiatkowski et al., *Calcif. Tiss. Int.*, 37:560–567 (1985); Kosher et al., *Dev. Biol.*, 118:112–117 (1986); and Chen et al., *Calcif. Tissue Int.*, 37:395–400 (1985)). In the hypertrophic region of the growth plate, proliferation ceases and a significant increase in cell volume, up to 8-fold, occurs. Hypertrophic chondrocytes form arcades and initiate the synthesis of type X collagen, while collagen types II and IX and proteoglycan content decrease. In the most inferior part of the growth plate, adjacent to the metaphysis, the cartilage mineralizes. Hypertrophic chondrocytes in the calcified tissue may undergo apoptosis (Shapiro et al., *J. Bone Min. Res.*, 10(S1):S238 (1995); Fujita et al., *Trans. Ann. Mtg. Othop. Res. Soc.*, 20:470 (1995); and Farnum et al., *Trans. Ann. Mtg. Othop. Res. Soc.*, 20:77 (1995)), partially convert to an osteoblastic phenotype (Cancedda et al., *J. Cell Biol.*, 117:427–435 (1992)), or remain quiescent until resorption by the invading blood vessels. The signals necessary for calcification are poorly understood, but calcification appears to be effected through the production of matrix vesicles, which contain alkaline phosphatase, phospholipase $A_2$, NTP-pyrophosphohydrolase, calcium, phosphate, and matrix metalloproteases (Dean et al., *Calcif. Tissue Int.*, 50:342–349 (1992); Lewinson et al., *J. Histochem. and Cytochem.*, 30:261–26 (1982); Wuthier et al., *Cal. Tissue Int.*, 24:163–171 (1977); and Watkins et al., *Biochem. Biophys. Acta*, 631:289–304 (1980)). The calcified cartilage serves as a scaffold for vascular invasion and deposition of the primary spongiosa.

A variety of cell culture models have been utilized to study the developmental changes associated with endochondral ossification. Embryonic chondrocytes from sterna (Leboy et al., *J. Biol. Chem.*, 264:17281–17286 (1989) ("Leboy"); Sullivan et al., *J. Biol. Chem.*, 269:22500–22506 (1994) ("Sullivan"); and Bohme et al., *Exp. Cell Res.*, 216:191–198 (1995) ("Bohme")), and vertebra (Lian et al., *J. Cellular Biochem.*, 52:206–219 (1993) ("Lian")), limb bud mesenchymal cells in micromass cultures (Roark et al., *Develop. Dynam.*, 200:103–116 (1994) ("Roark") and Downie et al., *Dev. Biol.*, 162:195 (1994) ("Downie")), growth plate chondrocytes in monolayer (Rosselot et al., *J. Bone Miner. Res.*, 9:431–439 (1994) ("Rosselot"); Gelb et al., *Endocrinology*, 127:1941–1947 (1990) ("Gelb"); and Crabb et al. *J. Bone Mineral Res.*, 5:1105–1112 (1990) ("Crab")), or pellet cultures (Kato et al., *Proc. Nat. Acad. Sci.*, 85:9552–9556 (1988) ("Kato")) have been used to characterize chondrocyte responses to exogenous factors, many of which function in an autocrine manner. From these studies has emerged a critical role for a number of growth factors, including bFGF, TGFβ, IGF-I, and PTHrP, which are present in the growth plate and regulate chondrocyte proliferation and differentiation. The expression of these factors and their associated receptors are maturation dependent and exquisitely regulated in the growth plate (Bohme, Roark, Rosselot, Gelb, Crabb, and Hill et al., *Prog. Growth Factor Res.*, 4:45–68 (1992)). Other studies have shown that vitamins A, C, and D are also required for chondrocyte maturation (Leboy; Sullivan; Iwamoto et al., *Microscopy Res. and Technique*, 28:483–491 (1994); Iwamoto et al., *Exp. Cell Res.*, 207:413–420 (1993); Iwamoto et al., *Exp. Cell Res.*, 205:213–224 (1993); Pacifici et al., *Exp. Cell Res.*, 195:38–46 (1991); Shapiro et al., *J. Bone Min. Res.*, 9:1229–1237 (1994); Corvol et al., *FEBS Lett.*, 116:273–276 (1980); Gerstenfeld et al., *Conn. Tiss. Res.*, 24:29–39 (1990); Schwartz et al., *J. Bone Miner. Res.*, 4:199–207 (1989); and Suda, *Calcif Tissue Int.*, 37:82–90 (1985)).

Transgenic mice and human cartilage defects have also provided information about endochondral ossification. Transgenic mice with deletions of the PthrP gene show premature hypertrophy of growth plate chondrocytes, demonstrating a role for PTHrP in cell proliferation and suppression of hypertrophy (Karaplis et al., *Genes and Develop.*, 8:227–289 (1994)). Human mutations in the collagens II, IX, X, and XI are the genetic bases for mild to severe (lethal) cartilage dysplasias (Kivirikko et al., *Ann. Rev. Biochem.*, 64:403–434 (1995)). Roles for sulfate transport (Hastabacka et al., *Cell*, 78:1074–1087 (1994)), sulfate metabolism (Franco et al., *Cell*, 81:15–25 (1995)), FGF receptor 3 (Shiang R. et al., *Cell*, 78:335–42 (1994)), and the transcription factor SOX9 (Wagner et al., *Cell*, 79:1111–1120 (1994)) in normal cartilage development have all been demonstrated by identification of genetic defects in human families.

The FGF receptor, sulfate transporters, and SOX9 are among the few examples of cellular proteins that have demonstrated roles in cartilage development. As outlined above, many of the proteins with critical roles in cartilage biology are either extracellular matrix proteins or signalling molecules. Thus, the genes and gene products instrumental to regulating the transition of chondrocytes from one stage to the next have yet to be fully characterized. Biochemical techniques used to identify matrix or intracellular components may not be sensitive enough to detect weakly or transiently expressed proteins. Furthermore, identification of cartilage defects in human or mouse mutants as a method to identify important cartilage or chondrocyte-specific proteins is limited by the number of mutants available and the labor involved in combined genetic and molecular approaches.

The present invention is directed to overcoming these and other deficiencies in the art.

SUMMARY OF THE INVENTION

The present invention relates to an isolated protein or polypeptide selectively expressed in chondrocytes in lower proliferative or upper hypertrophic zones of long bones and embryonic vertebrae growth plates. The encoding DNA molecule, in either isolated form or incorporated in a heterologous (i.e. not normally containing the DNA molecule of the present invention) expression system or a host cell, is also disclosed.

The present invention also relates to an antibody or binding portion thereof or probe with recognizes the protein or polypeptide.

Another aspect of the present invention relates to a method of identifying the occurrence of proliferation or hypertrophy of chondrocytes in a tissue sample. The sample is contacted with either the subject antibody, binding portion thereof, or probe; a nucleotide sequence of the DNA molecule encoding the subject protein or polypeptide as a probe in a nucleic acid hybridization assay; or a nucleotide sequence of the DNA molecule encoding the subject protein or polypeptide as a probe in a gene amplification detection procedure. An assay system is used to detect any reaction which indicates that an isolated protein or polypeptide selectively expressed in chondrocytes in lower proliferative or upper hypertrophic zones of long bones and embryonic vertebrae growth plates is present in the sample.

The present invention also relates to a method for preventing chondrocytes from transitioning from proliferation to hypertrophy and to a method for inhibiting arthritic progression of articular chondrocytes in a patient. These methods include reducing expression in the chondrocytes of a protein or polypeptide that is selectively expressed in chondrocytes in lower proliferative or upper hypertrophic zones of long bone and embryonic vertebrae growth plates. The present invention also relates to a method for inducing chondrocytes to transition from proliferation to hypertrophy and a method for treating non-union bone defects. These methods include increasing expression in the chondrocytes of a protein or a polypeptide selectively expressed in chondrocytes in lower proliferative or upper hypertrophic zones of long bone and embryonic vertebrae growth plates.

BRIEF DESCRIPTION OF THE DRAWINGS

In FIG. 1A, five micrograms of total RNA from growth plate and articular chondrocytes were loaded onto multiple pairs of lanes of a formaldehyde gel, electrophoresed, then transferred to GeneScreen Plus. Adjacent pairs were then hybridized with three different Band 17 cDNA fragments labeled with $^{32}$P. Location of probes I, II, and IV within Band 17 cDNAs is given in the legend for FIG. 5. FIG. 1B shows the results of an RNAase protection analysis of Band 17 expression of the 2.2 and 5.0 kb transcripts in chicken tissue. Riboprobes from the 260 bp cDNA template (probe II) were hybridized to 10 µg total RNA prepared from a variety of tissues from juvenile chick. Protected RNA fragments were separated on denaturing acrylamide gel and analyzed by autoradiography. Lanes contain RNA from brain (B); articular chondrocytes (A); growth plate chondrocytes (G), heart (H), Kidney (K), liver (L), lung (N), skeletal muscle (M), skin (S), and spleen (P). Glyceraldehyde-3-phosphate dehydrogenase ("GAPDH") is used as a control and is pictured under the Band 17 samples. Yeast tRNA did not give a protected fragment. UP designates the position of the undigested (full length) probe RNA (lane not shown), and PP designates the position of the protected band. FIG. 1C depicts the results of a RNAase protection analysis of the 5.0 and 6.2 kb transcripts. The same samples were used as described with regard to FIG. 1B. Separate tissue RNA samples were hybridized to either a 5.0 kb specific cRNA (probe III, FIG. 5), a 6.2 kb-specific cRNA probe (probe IV), or a GAPDH probe. Note that the GAPDH control indicates that the liver and muscle RNAs were in significant excess compared to the growth plate chondrocyte sample.

FIG. 2 depicts an in situ hybridization used to examine Band 17 expression in the long bone growth plates of 6–8 week chicks and the developing bones of 18 day chick embryos. The sections were hybridized with a $^{33}$P-labeled riboprobe that hydridizes to all Band 17 transcripts (Probe I in FIG. 5). Hybridization conditions were 50% formamide, 2×SSC at 56° C. Wash conditions were 68° C. in 0.1×SSC. Light field and dark field photomicrographs were taken of identical sections. R, P, and H in the light field photomicrographs designate the resting, proliferating, and hypertrophic zones of the growth plates.

FIG. 3 is an RNAase protection analysis of Band 17 expression performed in cultured sternal chondrocytes. Additions to the media were either NuSerum ("NSM") and/or ascorbate ("ASC"). The template for the RNA probe corresponds to probe I in FIG. 5, and hybridizes to all Band 17 transcripts. Y designates the lane containing probe hybridized to yeast tRNA. UP and PP designate the position of full length probe and protected fragment.

FIGS. 4A–4C show the time course of Band 17 expression in juvenile chicken growth plate chondrocytes in culture. FIG. 4A is an RNAase protection analysis of Band 17 expression in growth plate ("GP") cells. Samples were either five µg RNA from freshly isolated juvenile growth plate tissue (lane F), five µg RNA from enzymatically released chondrocytes (lane U), or yeast tRNA (lane Y). The template for the RNA probe corresponds to probe II in FIG. 5 and recognizes the 2.2 and 5.0 kb transcripts. 0.25 µg RNA was hybridized to the GAPDH probe as a loading control. UP and PP designate the position of full length probe and protected fragment. FIG. 4B shows the RNAase protection of Band 17 expression by cultured juvenile long bone chondrocytes. The chondrocytes were enzymatically released from the matrix and plated. Sample U (unplated) is RNA extracted from a cell pellet prior to plating. Lanes 1, 2 and 3 are RNA samples extracted from chondrocytes growing in monolayer for 1, 2 and 3 days. FIG. 4C is a Northern Blot analysis of the expression of collagen types II and X with β-actin as a control. The sample RNA from unplated and cultured chondrocytes is identical to the RNA used for Band 17 analysis in FIG. 4B.

FIG. 5 is a schematic diagram of Band 17 sequences, showing the alternative use of exons to form the 2.2, 5.0, and 6.2 kb cDNAs. Question marks represent unknown cDNA and genomic sequences. A, B, C, D, and E represent exons. The 5.0 kb transcript includes exons A–D, the 6.2 kb transcript includes exons A–C, plus E. The 2.2 kb transcript contains exons A–C and only the first part of exon D ($D_s$). Restriction sites are labeled below the genomic sequence diagram; Bg=BglII, X=XbaI, E=EcoRI, and Nc=NcoI. Thick bars represent cDNA fragments used as probes to analyze b17 mRNA expression and genomic structure. Probe I is the 0.25 kb PstI-BglII fragment that detects all transcripts (nt positions 106–354 in cDNA sequence given in FIG. 7). Probe II is the 0.26 kb fragment that detects the 2.2 and 5.0 kb transcripts (nt positions 4541–4800 in genomic sequence, Genbank Accession No. U59420) to be submitted to Genbank). Probe III is the 0.41 kb fragment that detects only the 5.0 kb transcript (nt positions 7413–7837 in genomic sequence). Probe IV is the 0.33 kb XmnI-KpnI fragment that detects only the 6.2 kb transcript (nt positions 634–966 in FIG. 7). Probe V is the 0.7 kb fragment used as a probe for genomic Southern Blots (nt positions 4391–5089 in genomic sequence).

In FIG. 6A, the blot was probed with a 700 bp fragment, corresponding to probe V in FIG. 5. In FIG. 6B, the same blot was stripped and reprobed with probe IV (specific to 6.2 kb cDNA). The position of size standards is indicated on the right.

FIG. 7 shows the cDNA sequence for the 6.2 kb transcript (nt 447 to nt 1526 of SEQ. ID. No. 6) with the predicted translation (aa 123 to aa 449 of SEQ. ID. No. 7). The reading frame within the 5.0 and 2.2 kb transcripts is congruous with that of the 6.2 kb transcript to position 587, which is the alternative splice point. The remainder of the 5.0 kb transcript is depicted schematically as exon D in FIG. 5 and starts at position 3948 in the genomic sequence. Relevant restriction sites are underlined and labeled. Potential N-glycosyslation sites are underlined in the amino acid sequence. Exons are labels in outlined letters that correspond to the exons shown in FIG. 5.

FIG. 8A compares the nucleotide homology between the chicken b17 sequence (upper sequence, identified herein as SEQ. ID. No. 9) and combined human cDNA sequences from the national sequence data bank ("NCBI") The human sequence (lower sequence, identified herein as SEQ. ID. No. 10) was derived from taking nt#1–#268 of clone c-3af01, Accession Number F12482, then adding 187 nt of clone c-1xb01, starting at position 182. Numbering for the chicken sequence is as shown in FIG. 7.

FIG. 8B compares the homology of predicted amino acid sequences for the chicken and human b17. The upper (chicken) and lower (human) amino acid sequences in FIG. 8B are identified herein as SEQ. ID. No. 11 and SEQ. ID. No. 12, respectively.

DETAILED DESCRIPTION OF THE INVENTION

Figure 1A:
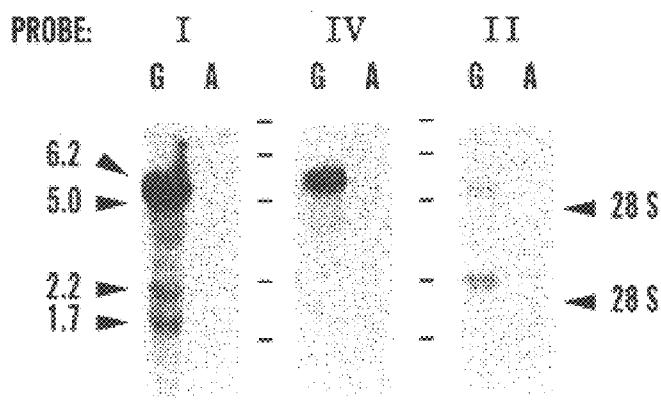
FIG. 1A is a Northern Blot hybridization.

The present invention relates to isolated DNA molecules encoding proteins or polypeptides selectively expressed in chondrocytes in lower proliferative or upper hypertrophic zones of long bone and embryonic vertebrae growth plates. These DNA molecules can also have the following characteristics: (1) expression of these DNA molecules is predominantly found in cartilage destined for mineralization, and their transcription products is undetectable in articular cartilage and undetectable or weak in kidney, liver, lung, skin, spleen, brain, heart, and muscle tissue; (2) expression of these DNA molecules is increased by induction of a hypertrophic phenotype in progenitor sternal chondrocytes by treatment with ascorbate; and (3) these DNA molecules are transcribed to form mRNA which exhibits a rapid but transient rise when hypertrophy is induced in growth plate chondrocytes in short term monolayer cultures.

One such DNA molecule comprises the nucleotide sequence corresponding to SEQ. ID. No. 1 as follows:

| | | | | |
|---|---|---|---|---|
| GATCACTGCG | ACAAGTTCGT | GGCCTTCGTG | GAGGACAACG | ACACAGCCAT |
| GTACCAAGTG | AACGCCTTCA | AAGAGGGCCC | GGAGATGAGG | AAGGTGTTGG |
| AGAAGGTGGC | GAGTGCCCTG | TGTCTGCCGG | CCAGCGAGCT | GAACGCAGGT |
| AACAGAGCGG | CCCCGGGTAC | GCTGCGCTCA | GTGTGATGCG | GGATGTGCTG |
| CAGTTATGCA | GAGTTCCTGT | CTAAAATACA | AGCTGAACCA | GATGCAGTCA |
| TGCAGGGTTC | GTGTGGGGCT | GCAGTAGTGC | GTGCTTGTTA | GTCAACAGAA |
| AGAAAACACC | TTTGGGAGTA | TCTTTCTTGG | AGACGAGTGG | AAGTATCAGC |
| TGTACCTTTG | TTTTAAGGGC | TCAGCTTTAC | TTTTGCTTTG | AGTTATGAGT |
| GTGTTACCTT | TTAATTCTCC | TTCTGTAAAA | TGTTGCAATT | CAAGCATGCA |
| GATAGTTGAA | GGGAAGGGAG | GATGTGTCTG | CGTTGTACCT | TCGCTTGTCT |
| ACAGGGAGCA | CATTTCCCAT | GCTCAGGAAG | CCCCCAGAAA | TAAGCACTGC |
| TGTCATTTCC | AGCATTCCCC | CAAAGATGTG | ATCCTAAAAC | CACGTCACGC |
| TGCAGCTCAA | ACCCAGCCAG | CAGCATACAG | GTTAAGCATG | GCAGCCTGAG |
| ACTGCTCCAC | AGTGAGCCGG | CACGCCTCCA | CCTGCCCCTC | TTCTGCCTTT |
| TGTGATAGTA | AGGCTATCCC | AGCAGTGGGA | CTATCACAGG | TGCATCAGTT |
| CAGTGTGGAA | TGTGTGGTTT | TGTTTCCCTG | AGGTTTGCAT | TCTGCACGAT |
| AACTCTATTG | GAAACTTTGT | TGCTTGGCAT | TTGGGCTGGT | GATTGTTTTC |
| AACCCTAAAT | TGTAGTTACT | CGTACAAAAC | CATGACAAGG | GGAAAGTTGG |
| GAGAAAGTTG | CTAGTTCTGT | GGTGGTGGTT | TTATCCCTTG | CTCCTTTCTT |
| GGATCTATTG | CAGATCTCGT | TCAAGTGGCT | TTCCTCACTT | GCTCGTATGA |
| GTTGGCTATA | AAAAATGTGA | CCTCCCCGTG | GTGTTCGCTC | TTCAGTGAAG |
| AAGATGCTAA | GGTAGGTGCT | AAATGCAGAG | GGCAGAGAGA | TTTGAGAAGC |
| CTTCAAAACA | TGCCTCACTG | TTTGGATGTT | GTTTTGTGGG | CAGTTGTAAG |
| TTCTGTGCCC | GTCCTTCTTC | AACCTTCATT | AGGTTTGGTG | CTCCATTAGC |
| GCTGCATTGG | TCTCCAAAGA | GCTGTGGGTT | AATCAAGCAG | TAGGACTGAA |
| ATACCTTCTG | CATTCAGACT | TAAATATTGG | CAGTGTCTTA | ATTTGTCCTG |
| ACTAAAATGA | TCTTTTCCAT | TGCACACTTA | ATTCATGTAA | TGCTTTTTC |
| TTTCTGTAAC | ACCTGAAATG | CTCTGGACAA | CTTTGTTTTA | CATGTATTAT |
| TTTTATATGA | TAAAATGTCT | TGATTTTAGA | GGACAGCAAA | TAAGGTCTTT |
| TAGGTCCTCT | GTGACTTCTT | TTCTGAGGCC | CAACTGGTCT | CTAATTCCTG |
| TTAATAAAAC | TAGTAGAACC | TGGATAAATA | TGACTTGCTT | TGGATTACTC |
| TTTGGAGGGA | TTGAGAGATT | TGGGGATTAA | GAATGATGCC | ATTTATTTGG |
| CACTGCAAAA | CACGTTTAGC | AATGCCCCTG | CAGAGGCTCC | TAAAGGAAGC |
| TTAGCAGCCC | TGCCAAAGAG | AAAAACCCTG | GAGTCAGGAG | GAAGCGGTCT |
| CCTCTCAAAG | AAGAGGAGGG | TCAGCAGGAA | TTTGTGCTGT | TTCCTTCTAA |
| TAGCTTAGTG | AGAGAGGAAA | GCTTGCTGAT | TAAGCGGTTA | CTTGGCACGT |
| TAAGAATATG | GGGTGTTTGA | GCAGCTCTGC | TGGAAGACTC | TACAAGGTTG |
| AATTGCCCAG | CAGTGCAGTG | GCAGTTGGTG | TTCAGTGTGA | AATTACGTGC |
| ATGGAGTAAG | AGGTTAAAGC | TCCATCAGTG | AGGTGGTGGG | CTCTCAGATC |
| CCTTTTTATT | ATTTATTTAT | TTATTTTCAC | TGTATGCAAT | AGTAAAAACT |
| TGTAAACTGT | GTTAACTTTA | GGTACTGGAG | TACCTGAATG | ACCTGAAGCA |

-continued

| | | | | |
|---|---|---|---|---|
| ATACTGGAAG | AGAGGATATG | GCTATGACAT | CAATAGTCGC | TCCAGCTGCA |
| TTTTATTCCA | GGATATCTTC | CAGCAGTTGG | ACAAAGCAGT | GGATGAGAGC |
| AGAAGGTAAA | TTAAAAAAAA | AAAAAGGGGG | GGGGGGGGGG | GAAGCTTTTG |
| TGTTGACTGA | CTGCAAGCTT | TCTGTGGTTA | ATCCTGAGTT | GGATTTGAGT |
| AGCAGTTAAA | CACTTCAGAC | ACAAGAATGC | TAGGAGAAGT | TTGGTTAGGA |
| GAACTTGTGA | TTAGAGAGAA | CAAAATCCTT | AATAGGATCG | TTACTGTAGA |
| GTGCAAATAG | GCTTGAGGTT | TTATTTTTCC | CATTGATGCT | TTTGTGCCCA |
| GTGGATTTAT | TTCCATCTTT | TAACTTACTG | ATCTGCACAG | GCCTTCAAAG |
| GACAGCCAGT | TACTGTGTCT | GACAGTGGTG | GTTTTTTCCT | GCTGAACAAT |
| GAATTTTTTG | TTTAAAATGT | CTTTGTTAAA | AAGCATTTGT | GGTGAAAGTG |
| GAAAGGCTGT | AGGTTAAAAA | AAGCAATATG | ATCGATTCTG | CTTTCTGGTT |
| ACTTAAACAC | TTCAGCATGA | AAGTCTTGTT | TTCTTTCCAT | GTGTGTTTGA |
| CATCTCTTGC | ACTATTAAAG | CTTTCTGAGC | TTTAAAGCTT | CAGGCTGAAG |
| GTGCTGAAAT | GCAATTACAA | AAGAATAATT | ATTTCAAGTG | AATCCAAACA |
| CTCAGTGACC | CTAGATGAGA | ACTGCCTGTT | GCAGAATCCA | CCAAGCCTGA |
| ACTGTAACAG | CAAACCAGCC | TTGTCATGCC | TGCTTCTTTG | TAACTGCAGA |
| AAGACAAACT | TAGGCAGTAT | ACTCGGTCCC | TGCACAAACA | GGAGAAAGGT |
| ACTTGAGCCC | TGAGGCTGTT | GTAAAAGCCT | TGGTTTGTTG | TACGAACATG |
| AGGCCAGTAA | TTTAGCCAGC | CAGCCACTCT | CTTAGATATT | TACTTTCGCA |
| TCCTTACTCA | TCTGCAGCAA | AACTGCCCAT | TGGGAGCAAT | GCTGTAGGTG |
| TAGGAAGTTG | TTAGACCTCA | CATGTATCTG | TTAGCAGACA | CAAAGATAGC |
| ACAAGCAAGA | GTCTGCAGAG | GAGGGTGGTC | TGATGAAGTG | GTTTGTGTTC |
| AGCTAGTTCC | ATGGTTTGGC | AAGTCATTTT | GTGTCAGAGA | AGGAAGAACA |
| GCAGTGGTAC | TCCTTCCAGG | AACTCTTACA | GCCCTCAAAA | TTGCCTTTAA |
| CGTGCCTTGG | AGGTACCTAT | GCTTCCTTAA | AAGCTAAAGA | CAAGATGCCT |
| GTGTTCTTGT | GTGTATTGTT | TACTCCTATC | AGCTGCTATC | AGTCGGCAGC |
| GGTGATCTGT | TGTAACCTAG | AGAAAACAGT | ATAGAAAACA | AAGGCTTTAG |
| TTACAGGTTT | GGGTGTTTAT | GTCACAAGAT | TAGCTGTATT | TGCTTTCATG |
| TGCCAGTAAT | AAAATTTTTG | AGAGCTGCGT | TAGGCTTAAA | AACAGTGCAT |
| GCATATGGGA | ATAATTTACA | ACCTGCATGA | ATGTTGTTTT | TCTAACAGAG |
| GAATTACAAA | TTCATAGCTT | AGTGATCAGC | CATGTGAATC | AGTACCTGAG |
| CAGGTAAGCG | CACAAATGTT | TACAAAAGCA | CACAAAATCA | AGGAGGTGAT |
| AACAAGATTG | TGTAAACATT | GTGCCTTTAA | ATGGTTCGTT | GGAATCAATG |
| TATGAGTAGC | GTAAGGTGAC | CAAGTTCAGC | TTTGATATTG | ATATAGAAAA |
| AGTAGTTGTA | TGTGATGGGT | GTACTTACAT | TGCTAGCATC | CTTGGGGTTC |
| TAGTTCTAAA | TTTAGGGTAC | TGAAGTAGGT | CAAAAATTAT | TTAGTGTTTC |
| AGGAACGAAA | GCTGAAGTCA | CTGATACTTG | AAGCTATATG | TGTGTATTTT |
| TTTTTACTTG | ATAACATGTA | AGAAAGCACT | TTATTTTCCC | CTGTCAGTTG |
| ACAGATTGAA | AATAGAGGTA | GCCTTGCAAT | TTTGGATCAG | AGGAATGATC |
| TATCAAATTG | TGAAGTCTTC | CTCCTTGGAA | GAAAAGCTTC | AAAAGCTGCC |

```
CTGGCACTAC  CCTGGGATAC  AGCCTCCAGA  GGTCCCTTCC  CACCTCAAGC
ATTCTGTAAC  GCCAATCACT  TCTTACAAAG  AGGACTGCGA  AGAAGTTGTT
CATCTAGATT  TTTGCTCACT  GAGGATCTGA  GTTAAATATC  AACAGTGATA
GAACTGACTG  TTAAGTCAGT  TGAAGCAGAA  TTCTCAGTCA  GTTGGCTTTT
TTGTTGTGCT  TCAGTGCTGG  ATGCAGAGAT  GCTGTGTGTT  AAGCCCTCTT
CATTTTGCTA  TGAACAGGCT  AGAACTTGTT  GTAAGCTAGT  TGTAAGCATG
AAACCAACAT  AGCACCGAGG  ACTAATTGTG  AAGGAAAGGT  GGGCAGAAGG
AAGTGGCTGT  TGATAGCAAA  CTCTCTGCAG  CAAGCCTGGA  CATTGTGCTG
CTAAATCATT  CTGGTTTTTG  GAAATCTAAG  GGCTGTCAGA  GCTGTTGATC
CCTCTCATTT  TGAGAGTGGT  GGAGTCAAAG  CTGTGGTTAT  GCTAGATTGC
CCTTTAAATA  AATCTCTACT  GTATCCTTTC  TTCAGCATTC  TGGGAAGCTA
AATAAAAAAT  GCATGAGGCC  ACAGGTCATT  TACATCCAAC  TGTGAAGAGA
TTGACAAGCA  CACTGCTGTG  ATTGCTTCCA  TATATGCTGT  GTCTGCTTCT
GCGAAGATAG  AAAATATAAA  CAGAATGAGG  AGACGAAGAG  CAGATTAAAA
GTGAGCAGAC  AAGCAGAGCA  AAACCCCTCT  GCCCTTCTGA  AGGAAAAAAA
AATAACTTCT  TAATGTAGCT  TGTCTCATAT  AAGGAGAATA  ATTAGATCTA
TTTGCTTTTA  GTGTATTTAT  TCTATGAGCA  GGGAAAGCCT  TTAAATCCTT
AAGTGCTACT  TAGAAAATAG  CTTTAATTCT  TAACTGTTTA  TTAAGTCTGT
AAGTTTAATA  ATGATAAAGC  TATAATTGAC  AAAATCCACA  TCTGTACTTC
CAGTTTATTG  ACAGCTCATT  CAGCAGCCCC  TAAATTTCTT  GGGAAGAGCA
GGTGTTGGAG  GCAGAGCAGT  AAAAGATTGA  GATGATCTCA  TCCTGTCTTA
GAGCTTTGGC  CATGGAATCA  GAATCACAGA  ATATCCCAAG  TTTGGAGGGA
TCTGTAAGGA  TCATCGAGTC  CAATTGTGAT  GTTTAAAACA  TGTCATTTAG
CAATGAGGTG  TTGAGGAGAA  GCAGTGAAGG  CCAGCAGATG  GATGTCTGTC
AGGATGGTCC  CTCCTGGTCA  CTGCTAGTCC  CTTCTTGTTT  GAAAGGAAAC
ACCCAAAATC  TCCACTGGTT  AAAACTTGTC  ACTAGAACCC  ATCTAGGAGA
GTCCTGAGCT  TCTGCTGATA  AGCTGTAAAA  TCAATTGTGA  TCAAACATGA
TCACAAGTGA  GACAATTCTA  GGGATGCCTG  GAGGGAAATG  ACCCACAGAG
GCCAAAATAC  AGGTATACAA  CTGGGGTTTT  CTACCTAAAC  TGAGGTGCTG
AGAGTTTGAA  CAGGCACCCT  ACCCTATAAC  ACCCTGTTGC  TCACCATGGA
TGGTGTTGCA  ATCCTTTTGA  ATTAAGCATG  TGGCTCCATG  AGGCTGGCAC
CAGTAAGCCA  GGACCTCCAA  ATGACAGAGT  ACAACTGATG  GAATCACTGA
GGTTTGAAGA  CACCTCTAAG  ACCATTGAGC  CCAACCAGCT  CATCCTTGAG
CTCCTGTGGC  TGCCCTCAGA  GCTGCTACAC  CCTCATCTCT  GTTCATTACC
AGGTTGTGAT  TATTTGGGAG  GAAGCTTGCC  TCCTCCTTCC  AGCCAGGAGA
GCCCTCTCAG  AGCATGGAAG  CAATTAGTAT  TTTCAGTCAA  TCCAATATAT
GCTGTCAGTC  TGCAAATAGC  CAACTAAACA  ACATGCCAGC  GTGCTGCCAT
GCTGTCAGTC  TGCAAATAGC  CAACTAAACA  ACTAGCCAGC  GTGCTGCCAG
TCCCCTTCTA  CGGACTGCTG  GTCTCCCAGG  GATAACTTCA  GGAAAGCTGT
TTCATTTGGG  AAAGTTATTC  CATGGCATCT  GCTGCAGGAC  ATACAGCTGA
GAGGGAGAAG  TCCTCCCAAG  CACAGGAGAA  CATCTCCCAT  CCTATGGAAG
```

-continued

```
CACCGAATTG  TGCAGGAGAT  AACCAACTGA  AAAACACAAA  CTTACATCCT

AACCCAGGGG  ATCATCTCCA  GTAGTCCAAT  TTTTGATAGA  CAAATGTAAG

TACAAATTTA  TGTCTGGTAA  AAGCCAAGAA  AATGGGTCAA  GCAAAATTTA

TCCAAAGCAC  ATTGTCTGAA  GAATGATGTG  ATATATTCAG  CAAAACCGAT

GTCAAGAAAT  TGACAGAAGT  TTAAAATAAT  AGCAGATGAC  TTCAGAGATT

TTCAGTGATT  TCTGGAATAT  ATTATAAAAG  CAAAAATATT  TGCACTGATC

TGTGATATTT  AAAGATGTAA  CTGGGAAGAA  TCACTGTTCA  GATGTGTTGT

TGTTACCCCA  GACAGAAGCA  GGTAGTGAGT  TTGTGCACAT  GTGTGGAGAG

TGGAGACCCT  GGCAAAAAAT  GGAGATCTGG  CAAAATTCAA  AGCTGGGTGA

GCAGCCTGCT  TACCCTGTGT  GTTCTAAAGT  GGGGGCTGAA  GGCATCTCAA

ACTTACTGCC  TTCTGCAAAA  CGAGCATGTA  ACCCCATCCC  GCAACGTCAG

GTGGCAGTAT  TAAAGCACTG  AAGGCTTGAG  TACAGTCTCT  ATTAGGCAAC

CTGGTTCACT  TAAAAGTAGG  TGGAAATCTA  CCACCACCAA  TGTAGGAGAG

CACCTTGTGT  CTCTTCATCT  GGGGAGTGGA  GATACAACTA  ACAATCCTTC

ATCTAGGGAG  GGAGACTTAT  GTGGGACCT   GAAGCAATTT  GAGAGTACAG

CTGAGAACAA  GAAACCATAC  AAAAGGAAAA  TATGCATATT  TTTTAGCCGT

AGAAAATACT  TGGTTGTGTA  TGCATGTGTT  ATTATGACTA  TATAGTGTTA

TTACTATATC  TTTAATGATA  TAGTACAGTT  CTGTATTTAA  TCTGTTGCCC

CACCTGCAGC  TGTTAATTGC  TCAGAAAATG  AGCCTCTGTG  GTGGCAAAAT

GTTGTCTTAT  TTATCCGTGT  TTTAACACTG  ATATATATCT  CTGGTTTGTT

CTGATACTAC  AGGAAGAATG  ATTTTATTTC  CAGAATCTTA  CTGTTGCTCC

AAGTTCTCCT  TTTTTTTTAA  AAATGAAAAG  TTTAGTTTGG  GCTATCCAGT

AGCAGCTGTT  GGAGCATTTG  TGCTCCAGCA  AGGAGTTATG  GTGTCTGGCT

TTGTGTTTCT  GTTCTAGGCT  TGTTGGTAGA  GAATGGCATT  GCCAGCTCTG

CATTTTATAG  CATATTTCAA  ATATTTATAT  TTAGCAGTTT  GCCCCGTTTT

CATTCCTTGT  TACAGCTCAA  ATAAAATGAG  AGCTTTTACT  TGTAACCCTT

TTTCTTCCAT  GAAGCTTTTA  TTGACCCAGC  AATCTGATTT  CTGATTATTT

GCCTAATTAG  TTGCCTTATT  AAAGCTCACT  CTTCTTTCTT  CTGGAAAAAG

TACCTTCTGG  AATAATGTCG  GCCCTTAAGA  AAATGATGAA  AATTACTGAA

ATTCTCAAGA  TTTTAACTAT  GAGACCATTA  GAGAGTTGGT  ATTTGAGTTA

CAACTTTGAT  GTCTCAGATG  TGAATGTTTG  GCGTCTCCAT  TCTTCTGCAC

CTTCAGTAGC  AATAAAACAT  TAATGTCCTG  TAAAGGTTAA  TTCCTTTTCT

TTGAGACCTT  ACCACTGTCA  AATAGGTTCT  TCCAAGACCA  CATTCCTCTG

TGTCTCCTTG  CCTGTCTGTA  AGGTGATACA  GTGATAACGT  GTCTGGGGAG

AGTTTGAGTG  CCACAACTCT  CCCATAAAAA  GTTTCTTATT  TAGAAGAAAA

AGGAAATAAT  ATTATAGGAG  TGGAGTAAAG  TTAAACCAGG  TGAGTTGTGC

TAAAATGGCA  TACTTGGGAA  GTTGTCCAAG  TCCAAATAAA  GAGCTTTATT

TTTGTGATAA  GGAAAGGATT  AAATTCTTCT  CATGTCTGTC  CGTTATGGAT

AGCCAACAAT  CAGACCATGC  AACTATATGG  CAAAGAAGCC  AATGGGGTAA

TACTCTTCTC  TGAACTGTTG  GTTTTTTTCC  ATACTGGAAC  CTTACAGAAA
```

-continued

```
ATGTCCCTAC   TCTTCATTAT   GTGGGCAAAA   CTGACAGGTA   GCGATGTGCT

TGTACTGCTG   CACTTGGCGT   TGTGCTGCTA   TGGAAGAATC   TCGAAAGGCT

GCTCTGCATT   TGATTGAAGA   GTTAGTGTCC   AATTTCCCAC   AGTTGTGGTA

TTTGGAGGAA   GTTTTAACAG   TGGTACATAG   AGGAGCAATA   GATGAGTGTC

TCTCTGCCTT   GGAAGAAGCT   T
```

Another such DNA molecule comprises the nucleotide sequence corresponding to SEQ. ID. No. 2 as follows:

```
GGCACGAAGG   GAGGCGAGAG   GATCCCGGAG   CAGCTGGAGC   AGGCGGCCGC

GCCCGTCCTC   CTCTTCCTGC   AGCTGCCGCC   ATGGCGCCGT   GCCGCGCTGC

CTGTCGTCTG   CCGCTTCTGG   TAGCGGTGGC   GAGCGCCGGG   CTGGGCGGCT

ACTTCGGCAC   CAAGTCCCGC   TACGAGGAGG   TGAACCCGCA   CCTGGCGGAG

GACCCGCTGT   CCCTCGGGCC   GCACGCCGCC   GCCGCCCGGC   TGCCCGCCGC

CTGCGCCCCG   CTGCAGCTCC   GCCGCGTCGT   CCGCCACGGC   ACCCGCTACC

CCACGGCCGG   GCAAATCCGC   CGCCTGGCCG   AGCTGCACGG   CCGCCTCCGC

CGCGCCGCCG   CCCCGTCCTG   CCCCGCCGCC   GCCGCGCTGG   CCGCCTGGCC

GATGTGGTAC   GAGGAGAGCC   TCGACGGGCG   GCTGGCGCCG   CGGGGCCGCC

GCGACATGGA   ACACCTGGCG   CGCCGCCTGG   CCGCCCGCTT   CCCCGCGCTC

TTCGCCGCCC   GCCGCCGCCT   GGCGCTGGCC   AGCAGCTCCA   AGCACCGCTG

CCTGCAGAGC   GGCGCGGCCT   TCCGGCGCGG   CCTCGGGCCC   TCCCTCAGCC

TCGGCGCCGA   CGAGACGGAG   ATCGAAGTGA   ACGACGCGCT   GATGAGGTTT

TTTGATCACT   GCGACAAGTT   CGTGGCCTTC   GTGGAGGACA   ACGACACAGC

CATGTACCAA   GTGAACGCCT   TCAAAGAGGG   CCCGGAGATG   AGGAAGGTGT

TGGAGAAGGT   GGCGAGTGCC   CTGTGTCTGC   CGGCCAGCGA   GCTGAACGCA

GATCTCGTTC   AAGTGGCTTT   CCTCACTTGC   TCGTATGAGT   TGGCTATAAA

AAATGTGACC   TCCCCGTGGT   GTTCGCTCTT   CAGTGAAGAA   GATGCTAAGG

TACTGGAGTA   CCTGAATGAC   CTGAAGCAAT   ACTGGAAGAG   AGGATATGGC

TATGACATCA   ATAGTCGCTC   CAGCTGCATT   TTATTCCAGG   ATATCTTCCA

GCAGTTGGAC   AAAGCAGTGG   ATGAGAGCAG   AAGTTGACAG   ATTGAAAATA

GAGGTAGCCT   TGCAATTTTG   GATCAGAGGA   ATGATCTATC   AAATTGTGAA

GTCTTCCTCC   TTGGAAGAAA   AGCTTCAAAA   GCTGCCCTGG   CACTACCCTG

GGATACAGCC   TCCAGAGGTC   CCTTCCCACC   TCAAGCATTC   TGTAACGCCA

ATCACTTCTT   ACAAAGAGGA   CTGCGAAGAA   GTTGTTCATC   TAGATTTTG

CTCACTGAGG   ATCTGAGTTA   AATATCAACA   GTGATAGAAC   TGACTGTTAA

GTCAGTTGAA   GCAGAATTCT   CAGTCAGTTG   GCTTTTTTGT   TGTGCTTCAG

TGCTGGATGC   AGAGATGCTG   TGTGTTAAGC   CCTCTTCATT   TTGCTATGAA

CAGGCTAGAA   CTTGTTGTAA   GCTAGTTGTA   AGCATGAAAC   CAACATAGCA

CCGAGGACTA   ATTGTGAAGG   AAAGGTGGGC   AGAAGGAAGT   GGCTGTTGAT

AGCAAACTCT   CTGCAGCAAG   CCTGGACATT   GTGCTGCTAA   ATCATTCTGG

TTTTTGGAAA   TCTAAGGGCT   GTCAGAGCTG   TTGATCCCTC   TCATTTGAG

AGTGGTGGAG   TCAAAGCTGT   GGTTATGCTA   GATTGCCCTT   TAAATAAATC
```

-continued

```
TCTACTGTAT  CCTTTCTTCA  GCATTCTGGG  AAGCTAAATA  AAAAATGCAT
GAGGCCACAG  GTCATTTACA  TCCAACTGTG  AAGAGATTGA  CAAGCACACT
GCTGTGATTG  CTTCCATATA  TGCTGTGTCT  GCTTCTGCGA  AGATAGAAAA
TATAAACAGA  ATGAGGAGAC  GAAGAGCAGA  TTAAAAGTGA  GCAGACAAGC
AGAGCAAAAC  CCCTCTGCCC  TTCTGAAGGA  AAAAAAAATA  ACTTCTTAAT
GTAGCTTGTC  TCATATAAGG  AGAATAATTA  GATCTATTTG  CTTTTAGTGT
ATTTATTCTA  TGAGCAGGGA  AAGCCTTTAA  ATCCTTAAGT  GCTACTTAGA
AAATAGCTTT  AATTCTTAAC  TGTTTATTAA  GTCTGTAAGT  TTAATAATGA
TAAAGCTATA  ATTGACAAAA  TCCACATCTG  TACTTCCAGT  TTATTGACAG
CTCATTCAGC  AGCCCCTAAA  TTTCTTGGGA  AGAGCAGGTG  TTGGAGGCAG
AGCAGTAAAA  GATTGAGATG  ATCTCATCCT  GTCTTAGAGC  TTTGGCCATG
GAATCAGAAT  CACAGAATAT  CCCAAGTTTG  GAGGGATCTG  TAAGGATCAT
CGAGTCCAAT  TGTGATGTTT  AAAACATGTC  ATTTAGCAAT  GAGGTGTTGA
GGAGAAGCAG  TGAAGGCCAG  CAGATGGATG  TCTGTCAGGA  TGGTCCCTCC
TGGTCACTGC  TAGTCCCTTC  TTGTTTGAAA  GGAAACACCC  AAAATCTCCA
CTGGTTAAAA  CTTGTCACTA  GAACCCATCT  AGGAGAGTCC  TGAGCTTCTG
CTGATAAGCT  GTAAAATCAA  TTGTGATCAA  ACATGATCAC  AAGTGAGACA
ATTCTAGGGA  TGCCTGGAGG  GAAATGACCC  ACAGAGGCCA  AAATACAGGT
ATACAACTGG  GGTTTTCTAC  CTAAACTGAG  GTGCTGAGAG  TTTGAACAGG
CACCCTACCC  TATAACACCC  TGTTGCTCAC  CATGGATGGT  GTTGCAATCC
TTTTGAATTA  AGCATGTGGC  TCCATGAGGC  TGGCACCAGT  AAGCCAGGAC
CTCCAAATGA  CAGAGTACAA  CTGATGGAAT  CACTGAGGTT  TGAAGCACCC
TCTAAGACCA  TTGAGCCCAA  CCAGCTCATC  CTTGAGCTCC  TGTGGCTGCC
CTCAGAGCTG  CTACACCCTC  ATCTCTGTTC  ATTACCAGGT  TGTGATTATT
TGGGAGGAAG  CTTGCCTCCT  CCTTCCAGCC  AGGAGAGCCC  TCTCAGAGCA
TGGAAGCAAT  TAGTATTTTC  AGTCAATCCA  ATATATGCTG  TCAGTCTGCA
AATAGCCAAC  TAAACAACAT  GCCAGCGTGC  TGCCATGCTG  TCAGTCTGCA
AATAGCCAAC  TAAACAACTA  GCCAGCGTGC  TGCCAGTCCC  CTTCTACGGA
CTGCTGGTCT  CCCAGGGATA  ACTTCAGGAA  AGCTGTTTCA  TTTGGGAAAG
TTATTCCATG  GCATCTGCTG  CAGGACATAC  AGCTGAGAGG  GAGAAGTCCT
CCCAAGCACA  GGAGAACATC  TCCCATCCTA  TGGAAGCACC  GAATTGTGCA
GGAGATAACC  AACTGAAAAA  CACAAACTTA  CATCCTAACC  CAGGGGATCA
TCTCCAGTAG  TCCAATTTTT  GATAGACAAA  TGTAAGTACA  AATTTATGTC
TGGTAAAAGC  CAAGAAAATG  GGTCAAGCAA  AATTTATCCA  AAGCACATTG
TCTGAAGAAT  GATGTGATAT  ATTCAGCAAA  ACCGATGTCA  AGAAATTGAC
AGAAGTTTAA  AATAATAGCA  GATGACTTCA  GAGATTTTCA  GTGATTTCTG
GAATATATTA  TAAAAGCAAA  AATATTTGCA  CTGATCTGTG  ATATTTAAAG
ATGTAACTGG  GAAGAATCAC  TGTTCAGATG  TGTTGTTGTT  ACCCCAGACA
GAAGCAGGTA  GTGAGTTTGT  GCACATGTGT  GGAGAGTGGA  GACCCTGGCA
AAAAATGGAG  ATCTGGCAAA  ATTCAAAGCT  GGGTGAGCAG  CCTGCTTACC
```

| | | | | |
|---|---|---|---|---|
| CTGTGTGTTC | TAAAGTGGGG | GCTGAAGGCA | TCTCAAACTT | ACTGCCTTCT |
| GCAAAACGAG | CATGTAACCC | CATCCCGCAA | CGTCAGGTGG | CAGTATTAAA |
| GCACTGAAGG | CTTGAGTACA | GTCTCTATTA | GGCAACCTGG | TTCACTTAAA |
| AGTAGGTGGA | AATCTACCAC | CACCAATGTA | GGAGAGCACC | TTGTGTCTCT |
| TCATCTGGGG | AGTGGAGATA | CAACTAACAA | TCCTTCATCT | AGGGAGGGAG |
| ACTTATGTGG | GGACCTGAAG | CAATTTGAGA | GTACAGCTGA | GAACAAGAAA |
| CCATACAAAA | GGAAAATATG | CATATTTTTT | AGCCGTAGAA | AATACTTGGT |
| TGTGTATGCA | TGTGTTATTA | TGACTATATA | GTGTTATTAC | TATATCTTTA |
| ATGATATAGT | ACAGTTCTGT | ATTTAATCTG | TTGCCCCACC | TGCAGCTGTT |
| AATTGCTCAG | AAAATGAGCC | TCTGTGGTGG | CAAAATGTTG | TCTTATTTAT |
| CCGTGTTTTA | ACACTGATAT | ATATCTCTGG | TTTGTTCTGA | TACTACAGGA |
| AGAATGATTT | TATTTCCAGA | ATCTTACTGT | TGCTCCAAGT | TCTCCTTTTT |
| TTTTAAAAAT | GAAAAGTTTA | GTTTGGGCTA | TCCAGTAGCA | GCTGTTGGAG |
| CATTTGTGCT | CCAGCAAGGA | GTTATGGTGT | CTGGCTTTGT | GTTTCTGTTC |
| TAGGCTTGTT | GGTAGAGAAT | GGCATTGCCA | GCTCTGCATT | TTATAGCATA |
| TTTCAAATAT | TTATATTTAG | CAGTTTGCCC | CGTTTTCATT | CCTTGTTACA |
| GCTCAAATAA | AATGAGAGCT | TTTACTTGTA | ACCCTTTTC | TTCCATGAAG |
| CTTTTATTGA | CCCAGCAATC | TGATTTCTGA | TTATTTGCCT | AATTAGTTGC |
| CTTATTAAAG | CTCACTCTTC | TTTCTTCTGG | AAAAAGTACC | TTCTGGAATA |
| ATGTCGGCCC | TTAAGAAAAT | GATGAAAATT | ACTGAAATTC | TCAAGATTTT |
| AACTATGAGA | CCATTAGAGA | GTTGGTATTT | GAGTTACAAC | TTTGATGTCT |
| CAGATGTGAA | TGTTTGGCGT | CTCCATTCTT | CTGCACCTTC | AGTAGCAATA |
| AAACATTAAT | GTCCTGTAAA | GGTTAATTCC | TTTTCTTTGA | GACCTTACCA |
| CTGTCAAATA | GGTTCTTCCA | AGACCACATT | CCTCTGTGTC | TCCTTGCCTG |
| TCTGTAAGGT | GATACAGTGA | TAACGTGTCT | GGGGAGAGTT | TGAGTGCCAC |
| AACTCTCCCA | TAAAAAGTTT | CTTATTTAGA | AGAAAAAGGA | AATAATATTA |
| TAGGAGTGGA | GTAAAGTTAA | ACCAGGTGAG | TTGTGCTAAA | ATGGCATACT |
| TGGGAAGTTG | TCCAAGTCCA | AATAAAG | | |

This DNA molecule encodes for a protein or polypeptide having a molecular weight from about 34 to 40 kDa, preferably about 37 kDa, and having an amino acid sequence corresponding to SEQ. ID. No. 3 as follows:

| | | | | |
|---|---|---|---|---|
| MAPCRAACLL | PLLVAVASAG | LGGYFGTKSR | YEEVNPHLAE | DPLSLGPHAA |
| AARLPAACAP | LQLRRVVRHG | TRYPTAGQIR | RLAELHGRLR | RAAAPSCPAA |
| AALAAWPMWY | EESLDGRLAP | RGRRDMEHLA | RRLAARFPAL | FAARRRLALA |
| SSSKHRCLQS | GAAFRRGLGP | SLSLGADETE | IEVNDALMRF | FDHCDKFVAF |
| VEDNDTAMYQ | VNAFKEGPEM | RKVLEKVASA | LCLPASELNA | DLVQVAFLTC |
| SYELAIKNVT | SPWCSLFSEE | DAKVLEYLND | LKQYWKRGYG | YDINSRSSCI |
| LFQDIFQQLD | KAVDESRS | | | |

Another such DNA molecule comprises the nucleotide sequence corresponding to SEQ. ID. No. 4 as follows:

| | | | | |
|---|---|---|---|---|
| GGCACGAAGG | GAGGCGAGAG | GATCCCGGAG | CAGCTGGAGC | AGGCGGCCGC |
| GCCCGTCCTC | CTCTTCCTGC | AGCTGCCGCC | ATGGCGCCGT | GCCGCGCTGC |
| CTGTCGTCTG | CCGCTTCTGG | TAGCGGTGGC | GAGCGCCGGG | CTGGGCGGCT |
| ACTTCGGCAC | CAAGTCCCGC | TACGAGGAGG | TGAACCCGCA | CCTGGCGGAG |
| GACCCGCTGT | CCCTCGGGCC | GCACGCCGCC | GCCGCCCGGC | TGCCCGCCGC |
| CTGCGCCCCG | CTGCAGCTCC | GCCGCGTCGT | CCGCCACGGC | ACCCGCTACC |
| CCACGGCCGG | GCAAATCCGC | CGCCTGGCCG | AGCTGCACGG | CCGCCTCCGC |
| CGCGCCGCCG | CCCCGTCCTG | CCCCGCCGCC | GCCGCGCTGG | CCGCCTGGCC |
| GATGTGGTAC | GAGGAGAGCC | TCGACGGGCG | GCTGGCGCCG | CGGGGCCGCC |
| GCGACATGGA | ACACCTGGCG | CGCCGCCTGG | CCGCCCGCTT | CCCCGCGCTC |
| TTCGCCGCCC | GCCGCCGCCT | GGCGCTGGCC | AGCAGCTCCA | AGCACCGCTG |
| CCTGCAGAGC | GGCGCGGCCT | TCCGGCGCGG | CCTCGGGCCC | TCCCTCAGCC |
| TCGGCGCCGA | CGAGACGGAG | ATCGAAGTGA | ACGACGCGCT | GATGAGGTTT |
| TTTGATCACT | GCGACAAGTT | CGTGGCCTTC | GTGGAGGACA | ACGACACAGC |
| CATGTACCAA | GTGAACGCCT | TCAAAGAGGG | CCCGGAGATG | AGGAAGGTGT |
| TGGAGAAGGT | GGCGAGTGCC | CTGTGTCTGC | CGGCCAGCGA | GCTGAACGCA |
| GATCTCGTTC | AAGTGGCTTT | CCTCACTTGC | TCGTATGAGT | TGGCTATAAA |
| AAATGTGACC | TCCCCGTGGT | GTTCGCTCTT | CAGTGAAGAA | GATGCTAAGG |
| TACTGGAGTA | CCTGAATGAC | CTGAAGCAAT | ACTGGAAGAG | AGGATATGGC |
| TATGACATCA | ATAGTCGCTC | CAGCTGCATT | TTATTCCAGG | ATATCTTCCA |
| GCAGTTGGAC | AAAGCAGTGG | ATGAGAGCAG | AAGTTGACAG | ATTGAAAATA |
| GAGGTAGCCT | TGCAATTTTG | GATCAGAGGA | ATGATCTATC | AAATTGTGAA |
| GTCTTCCTCC | TTGGAAGAAA | AGCTTCAAAA | GCTGCCCTGG | CACTACCCTG |
| GGATACAGCC | TCCAGAGGTC | CCTTCCCACC | TCAAGCATTC | TGTAACGCCA |
| ATCACTTCTT | ACAAAGAGGA | CTGCGAAGAA | GTTGTTCATC | TAGATTTTTG |
| CTCACTGAGG | ATCTGAGTTA | AATATCAACA | GTGATAGAAC | TGACTGTTAA |
| GTCAGTTGAA | GCAGAATTCT | CAGTCAGTTG | GCTTTTTTGT | TGTGCTTCAG |
| TGCTGGATGC | AGAGATGCTG | TGTGTTAAGC | CCTCTTCATT | TTGCTATGAA |
| CAGGCTAGAA | CTTGTTGTAA | GCTAGTTGTA | AGCATGAAAC | CAACATAGCA |
| CCGAGGACTA | ATTGTGAAGG | AAAGGTGGGC | AGAAGGAAGT | GGCTGTTGAT |
| AGCAAACTCT | CTGCAGCAAG | CCTGGACATT | GTGCTGCTAA | ATCATTCTGG |
| TTTTTGGAAA | TCTAAGGGCT | GTCAGAGCTG | TTGATCCCTC | TCATTTTGAG |
| AGTGGTGGAG | TCAAAGCTGT | GGTTATGCTA | GATTGCCCTT | TAAATAAATC |
| TCTACTGTAT | CCTTTCTTCA | GCATTCTGGG | AAGCTAAATA | AAAAATGCAT |
| GAGGCCACAG | GTCATTTACA | TCCAACTGTG | AAGAGATTGA | CAAGCACACT |
| GCTGTGATTG | CTTCCATATA | TGCTGTGTCT | GCTTCTGCGA | AGATAGAAAA |
| TATAAACAGA | ATGAGGAGAC | GAAGAGCAGA | TTAAAAGTGA | GCAGACAAGC |
| AGAGCAAAAC | CCCTCTGCCC | TTCTGAAGGA | AAAAAAAATA | ACTTCTTAAT |
| GTAGCTTGTC | TCATATAAGG | AGAATAATTA | GATCTATTTG | CTTTTAGTGT |
| ATTTATTCTA | TGAGCAGGGA | AAGCCTTTAA | ATCCTTAAGT | GCTACTTAGA |
| AAATAGCTTT | AATTCTTAAC | TGTTTATTAA | GTCTGTAAGT | TTAATAATGA |

| | | | | |
|---|---|---|---|---|
| TAAAGCTATA | ATTGACAAAA | TCCACATCTG | TACTTCCAGT | TTATTGACAG |
| CTCATTCAGC | AGCCCCTAAA | TTTCTTGGGA | AGAGCAGGTG | TTGGAGGCAG |
| AGCAGTAAAA | GATTGAGATG | ATCTCATCCT | GTCTTAGAGC | TTTGGCCATG |
| GAATCAGAAT | CACAGAATAT | CCCAAGTTTG | GAG | |

This DNA molecule also encodes for a protein or polypeptide having a molecular weight of from about 34 to about 40 kDa, preferably about 37 kDa, and an amino acid sequence corresponding to SEQ. ID. No. 3 as provided above.

Another such DNA molecule comprises the nucleotide sequence corresponding to SEQ. ID. No. 5 as follows:

| | | | | |
|---|---|---|---|---|
| ATGGCGCCGT | GCCGCGCTGC | CTGTCGTCTG | CCGCTTCTGG | TAGCGGTGGC |
| GAGCGCCGGG | CTGGGCGGCT | ACTTCGGCAC | CAAGTCCCGC | TACGAGGAGG |
| TGAACCCGCA | CCTGGCGGAG | GACCCGCTGT | CCCTCGGGCC | GCACGCCGCC |
| GCCGCCCGGC | TGCCCGCCGC | CTGCGCCCCG | CTGCAGCTCC | GCCGCGTCGT |
| CCGCCACGGC | ACCCGCTACC | CCACGGCCGG | GCAAATCCGC | CGCCTGGCCG |
| AGCTGCACGG | CCGCCTCCGC | CGCGCCGCCG | CCCCGTCCTG | CCCCGCCGCC |
| GCCGCGCTGG | CCGCCTGGCC | GATGTGGTAC | GAGGAGAGCC | TCGACGGGCG |
| GCTGGCGCCG | CGGGGCCGCC | GCGACATGGA | ACACCTGGCG | CGCCGCCTGG |
| CCGCCCGCTT | CCCCGCGCTC | TTCGCCGCCC | GCCGCCGCCT | GGCGCTGGCC |
| AGCAGCTCCA | AGCACCGCTG | CCTGCAGAGC | GGCGCGGCCT | TCCGGCGCGG |
| CCTCGGGCCC | TCCCTCAGCC | TCGGCGCCGA | CGAGACGGAG | ATCGAAGTGA |
| ACGACGCGCT | GATGAGGTTT | TTTGATCACT | GCGACAAGTT | CGTGGCCTTC |
| GTGGAGGACA | ACGACACAGC | CATGTACCAA | GTGAACGCCT | TCAAAGAGGG |
| CCCGGAGATG | AGGAAGGTGT | TGGAGAAGGT | GGCGAGTGCC | CTGTGTCTGC |
| CGGCCAGCGA | GCTGAACGCA | GATCTCGTTC | AAGTGGCTTT | CCTCACTTGC |
| TCGTATGAGT | TGGCTATAAA | AAATGTGACC | TCCCCGTGGT | GTTCGCTCTT |
| CAGTGAAGAA | GATGCTAAGG | TACTGGAGTA | CCTGAATGAC | CTGAAGCAAT |
| ACTGGAAGAG | AGGATATGGC | TATGACATCA | ATAGTCGCTC | CAGCTGCATT |
| TTATTCCAGG | ATATCTTCCA | GCAGTTGGAC | AAAGCAGTGG | ATGAGAGCAG |
| AAGT | | | | |

This DNA molecule also encodes for a protein or polypeptide having a molecular weight of from about 34 to about 40 kDa, preferably about 37 kDa, and an amino acid sequence corresponding to SEQ. ID. No. 3 as provided above.

Another such DNA molecule comprises the nucleotide sequence corresponding to SEQ. ID. No. 6 as follows:

| | | | | |
|---|---|---|---|---|
| GGCACGAAGG | GAGGCGAGAG | GATCCCGGAG | CAGCTGGAGC | AGGCGGCCGC |
| GCCCGTCCTC | CTCTTCCTGC | AGCTGCCGCC | ATGGCGCCGT | GCCGCGCTGC |
| CTGTCGTCTG | CCGCTTCTGG | TAGCGGTGGC | GAGCGCCGGG | CTGGGCGGCT |
| ACTTCGGCAC | CAAGTCCCGC | TACGAGGAGG | TGAACCCGCA | CCTGGCGGAG |
| GACCCGCTGT | CCCTCGGGCC | GCACGCCGCC | GCCGCCCGGC | TGCCCGCCGC |
| CTGCGCCCCG | CTGCAGCTCC | GCCGCGTCGT | CCGCCACGGC | ACCCGCTACC |

-continued

```
CCACGGCCGG  GCAAATCCGC  CGCCTGGCCG  AGCTGCACGG  CCGCCTCCGC
CGCGCCGCCG  CCCCGTCCTG  CCCCGCCGCC  GCCGCGCTGG  CCGCCTGGCC
GATGTGGTAC  GAGGAGAGCC  TCGACGGGCG  GCTGGCGCCG  CGGGGCCGCC
GCGACATGGA  ACACCTGGCG  CGCCGCCTGG  CCGCCCGCTT  CCCCGCGCTC
TTCGCCGCCC  GCCGCCGCCT  GGCGCTGGCC  AGCAGCTCCA  AGCACCGCTG
CCTGCAGAGC  GGCGCGGCCT  TCCGGCGCGG  CCTCGGGCCC  TCCCTCAGCC
TCGGCGCCGA  CGAGACGGAG  ATCGAAGTGA  ACGACGCGCT  GATGAGGTTT
TTTGATCACT  GCGACAAGTT  CGTGGCCTTC  GTGGAGGACA  ACGACACAGC
CATGTACCAA  GTGAACGCCT  TCAAAGAGGG  CCCGGAGATG  AGGAAGGTGT
TGGAGAAGGT  GGCGAGTGCC  CTGTGTCTGC  CGGCCAGCGA  GCTGAACGCA
GATCTCGTTC  AAGTGGCTTT  CCTCACTTGC  TCGTATGAGT  TGGCTATAAA
AAATGTGACC  TCCCCGTGGT  GTTCGCTCTT  CAGTGAAGAA  GATGCTAAGG
TACTGGAGTA  CCTGAATGAC  CTGAAGCAAT  ACTGGAAGAG  AGGATATGGC
TATGACATCA  ATAGTCGCTC  CAGCTGCATT  TTATTCCAGG  ATATCTTCCA
GCAGTTGGAC  AAAGCAGTGG  ATGAGAGCAG  AAGTTCCAGG  ATATCTTCCA
GCAGTTGGAC  AAAGCAGTGG  ATGAGAGCAG  AAGTTCAAAA  CCCATTTCTT
CACCTTTGAT  TGTACAAGTT  GGACATGCAG  AAACACTTCA  GCCACTTCTT
GCTCTTATGG  GCTACTTCAA  AGATGCTGAG  CCTCTCCAGG  CCAACAATTA
CATCCGCCAG  GCGCATCGGA  AGTTCCGCAG  CGGCCGGATA  GTGCCTTATG
CAGCCAACCT  GGTGTTTGTG  CTGTACCACT  GTGAGCAGAA  GACCTCTAAG
GAGGAGTACC  AAGTGCAGAT  GTTGCTGAAT  GAAAAGCCAA  TGCTCTTTCA
TCACTCGAAT  GAAACCATCT  CCACGTATGC  AGACCTCAAG  AGCTATTACA
AGGACATCCT  TCAAAACTGT  CACTTCGAAG  AAGTGTGTGA  ATTGCCCAAA
GTCAATGGTA  CCGTTGCTGA  CGAACTTTGA  GGGAATGAAA  TGGAGTGGCC
GATTTGGAAA  CCGATCTCAG  TTTTCTTCAA  CAGATGTTGT  GAACGAGCAC
TTTGGATGCA  ATGCTGCTGC  TGTGCCGACT  CTCTAAGCTC  GCAGATTTGA
CGGCCGTTAT  TTACCTGGG   TTGTCTCTGTC  AGCTCAA
```

This DNA molecule encodes for a peptide having a molecular weight of from about 47 to about 53 kDa, preferably about 50 kDa, and has an amino acid sequence corresponding to SEQ. ID. No. 7 as follows:

```
MAPCRAACLL  PLLVAVASAG  LGGYFGTKSR  YEEVNPHLAE  DPLSLGPHAA
AARLPAACAP  LQLRRVVRHG  TRYPTAGQIR  RLAELHGRLR  RAAAPSCPAA
AALAAWPMWY  EESLDGRLAP  RGRRDMEHLA  RRLAARFPAL  FAARRRLALA
SSSKHRCLQS  GAAFRRGLGP  SLSLGADETE  IEVNDALMRF  FDHCDKFVAF
VEDNDTAMYQ  VNAFKEGPEM  RKVLEKVASA  LCLPASELNA  DLVQVAFLTC
SYELAIKNVT  SPWCSLFSEE  DAKVLEYLND  LKQYWKRGYG  YDINSRSSCI
LFQDIFQQLD  KAVDESRSSK  PISSPLIVQV  GHAETLQPLL  ALMGYFKDAE
PLQANNYIRQ  AHRKFRSGRI  VPYAANLVFV  LYHCEQKTSK  EEYQVQMLLN
EKPMLFHHSN  ETISTYADLK  SYYKDILQNC  HFEEVCELPK  VNGTVADEL
```

Another such DNA molecule comprises the nucleotide sequence corresponding to SEQ. ID. No. 8 as follows:

| | | | | |
|---|---|---|---|---|
| ATGGCGCCGT | GCCGCGCTGC | CTGTCGTCTG | CCGCTTCTGG | TAGCGGTGGC |
| GAGCGCCGGG | CTGGGCGGCT | ACTTCGGCAC | CAAGTCCCGC | TACGAGGAGG |
| TGAACCCGCA | CCTGGCGGAG | GACCCGCTGT | CCCTCGGGCC | GCACGCCGCC |
| GCCGCCCGGC | TGCCCGCCGC | CTGCGCCCCG | CTGCAGCTCC | GCCGCGTCGT |
| CCGCCACGGC | ACCCGCTACC | CCACGGCCGG | GCAAATCCGC | CGCCTGGCCG |
| AGCTGCACGG | CCGCCTCCGC | CGCGCCGCCG | CCCCGTCCTG | CCCCGCCGCC |
| GCCGCGCTGG | CCGCCTGGCC | GATGTGGTAC | GAGGAGAGCC | TCGACGGGCG |
| GCTGGCGCCG | CGGGGCCGCC | GCGACATGGA | ACACCTGGCG | CGCCGCCTGG |
| CCGCCCGCTT | CCCCGCGCTC | TTCGCCGCCC | GCCGCCGCCT | GGCGCTGGCC |
| AGCAGCTCCA | AGCACCGCTG | CCTGCAGAGC | GGCGCGGCCT | TCCGGCGCGG |
| CCTCGGGCCC | TCCCTCAGCC | TCGGCGCCGA | CGAGACGGAG | ATCGAAGTGA |
| ACGACGCGCT | GATGAGGTTT | TTTGATCACT | GCGACAAGTT | CGTGGCCTTC |
| GTGGAGGACA | ACGACACAGC | CATGTACCAA | GTGAACGCCT | TCAAAGAGGG |
| CCCGGAGATG | AGGAAGGTGT | TGGAGAAGGT | GGCGAGTGCC | CTGTGTCTGC |
| CGGCCAGCGA | GCTGAACGCA | GATCTCGTTC | AAGTGGCTTT | CCTCACTTGC |
| TCGTATGAGT | TGGCTATAAA | AAATGTGACC | TCCCCGTGGT | GTTCGCTCTT |
| CAGTGAAGAA | GATGCTAAGG | TACTGGAGTA | CCTGAATGAC | CTGAAGCAAT |
| ACTGGAAGAG | AGGATATGGC | TATGACATCA | ATAGTCGCTC | CAGCTGCATT |
| TTATTCCAGG | ATATCTTCCA | GCAGTTGGAC | AAAGCAGTGG | ATGAGAGCAG |
| AAGTTCAAAA | CCCATTTCTT | CACCTTTGAT | TGTACAAGTT | GGACATGCAG |
| AAACACTTCA | GCCACTTCTT | GCTCTTATGG | GCTACTTCAA | AGATGCTGAG |
| CCTCTCCAGG | CCAACAATTA | CATCCGCCAG | GCGCATCGGA | AGTTCCGCAG |
| CGGCCGGATA | GTGCCTTATG | CAGCCAACCT | GGTGTTTGTG | CTGTACCACT |
| GTGAGCAGAA | GACCTCTAAG | GAGGAGTACC | AAGTGCAGAT | GTTGCTGAAT |
| GAAAAGCCAA | TGCTCTTTCA | TCACTCGAAT | GAAACCATCT | CCACGTATGC |
| AGACCTCAAG | AGCTATTACA | AGGACATCCT | TCAAAACTGT | CACTTCGAAG |
| AAGTGTGTGA | ATTGCCCAAA | GTCAATGGTA | CCGTTGCTGA | CGAACTT |

This DNA molecule also encodes for a protein or polypeptide having a molecular weight of from about 47 to about 53 kDa, preferably about 50 kDa, and an amino acid sequence corresponding to SEQ. ID. No. 7 as provided above.

Also encompassed by the present invention are fragments of the DNA molecules of the present invention. These fragments are constructed by using appropriate restriction sites, revealed by inspection of the DNA molecules sequence to, for example, delete various internal portions of the encoded protein. Alternatively, the sequence can be used to amplify any portion of the coding region, such that it can be cloned into a vector supplying both transcription and translation start signals.

Variants may also (or alternatively) be modified by, for example, the deletion or addition of nucleotides that have minimal influence on the properties, secondary structure, and hydropathic nature of the encoded polypeptide. For example, the nucleotides encoding a polypeptide may be altered so that the encoded polypeptide is conjugated to a linker or other sequence for ease of synthesis, purification, or identification of the polypeptide.

The protein or polypeptide of the present invention is preferably produced in purified form (preferably, at least about 80%, more preferably 90%, pure) by conventional techniques. Typically, the protein or polypeptide of the present invention is isolated by homongenizing a host cell in which the protein is expressed, centrifuging to remove cellular debris, and precipitating the desired protein, such as with ammonium sulfate. The fraction containing the proteins of the present invention can be subjected affinity chromatography, ion exchange, or gel filtration to separate the protein. Optionally, the protein can be further purified by high performance liquid chromatography ("HPLC") or fast protein liquid chromatography ("FPLC").

Any one of the DNA molecules encoding for a protein or polypeptide selectively expressed in chondrocytes in lower proliferative or upper hypertrophic zones of long bone and embryonic vertebrae growth plates can be incorporated in cells using conventional recombinant DNA technology. Generally, this involves inserting the selected DNA molecule into an expression system to which that DNA molecule is heterologous (i.e. not normally present). The heterologous DNA molecule is inserted into the expression system or vector in proper orientation and correct reading frame. The vector contains the necessary elements for the transcription and translation of the inserted protein-coding sequences.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eukaryotic cells grown in tissue culture.

Recombinant genes may also be introduced into viruses, such as vaccina virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pRO-EX (Gibco/BRL), pBR322, pBR325, pACYC177, pACYC184, pUC8, pUC9, pUC18, pUC19, pLG339, pR290, pKC37, pKC101, SV 40, pBluescript II SK ± or KS ± (see "Stratagene Cloning Systems" Catalog (1993) from Stratagene, La Jolla, Calif., which is hereby incorporated by reference), pQE, pIH821, pGEX, pET series (see F. W. Studier et. al., "Use of T7 RNA Polymerase to Direct Expression of Cloned Genes," *Gene Expression Technology* vol. 185 (1990), which is hereby incorporated by reference) and any derivatives thereof. Recombinant molecules can be introduced into cells via transformation, particularly transduction, conjugation, mobilization, or electroporation. The DNA sequences are cloned into the vector using standard cloning procedures in the art, as described by Maniatis et al., *Molecular Cloning: A Laboratory Manual*, Cold Springs Laboratory, Cold Springs Harbor, N.Y. (1982), which is hereby incorporated by reference.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.) or stably transfected with an expression vector; and insect cell systems infected with virus (e.g., baculovirus). The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promoter which is a DNA sequence that directs the binding of RNA polymerase and thereby promotes mRNA synthesis. The DNA sequences of eukaryotic promoters differ from those of prokaryotic promoters. Furthermore, eucaryotic promoters and accompanying genetic signals may not be recognized in or may not function in a procaryotic system, and, further, procaryotic promoters are not recognized and do not function in eucaryotic cells.

Similarly, translation of mRNA in prokaryote depends upon the presence of the proper procaryotic signals which differ from those of eukaryotes. Efficient translation of mRNA in prokaryote requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference.

Promoters vary in their "strength" (i.e. their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operon, the addition of specific inducers is necessary for efficient transcription of the inserted DNA. For example, the lac operon is induced by the addition of lactose or IPTG (isopropylthio-beta-D-galactoside). A variety of other operon, such as trp, pro, etc., are under different controls.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires a Shine-Dalgarno ("SD") sequence about 7–9 bases 5' to the initiation codon (ATG) to provide a ribosome binding site. Thus, any SD-ATG combination that can be utilized by host cell ribosomes may be employed. Additionally, any SD-ATG combination produced by recombinant DNA or other techniques involving incorporation of synthetic nucleotides may be used.

Once the desired isolated DNA molecule encoding an isolated protein or polypeptide selectively expressed in chondrocytes in lower proliferative or upper hypertrophic zones of long bone and embryonic vertebrae growth plates has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, and the like.

Generally there are numerous genes differentially expressed within the growth plate. However, genes selectively expressing proteins or polypeptides in chondrocytes of lower proliferative or upper hypertrophic zones of long bone and embryonic vertebrae growth plates are very rare. In view of the present invention's determination of nucleotide sequences corresponding to proteins which are selectively expressed in chondrocytes in lower proliferative or upper hypertrophic zones, and further in view of the importance of lower proliferative or upper hypertrophic zone chondrocytes in normal bone development and the deleterious affects of chondrocytes proliferation and hypertrophy in certain osteopathic syndromes, such as arthritis, the molecular basis for chondrocyte proliferation and hypertrophy is suggested. With this information and the above-described recombinant DNA technology, a wide variety of therapeutic and prophylactic agents for inducing or preventing chondrocyte transition from proliferation to hypertrophy can be developed. In addition, the present invention permits the development of diagnostic procedures for identifying the occurrence of proliferation or hypertrophy or the transition of chondrocytes from proliferation to hypertrophy in a tissue sample.

For example, the proteins or polypeptides of the present invention can be used to raise antibodies or binding portions thereof. These antibodies are useful in diagnostic assays for the identification of the occurrence of proliferation or hypertrophy of chondrocytes in a tissue sample.

Antibodies suitable for use in identifying the occurrence of proliferation or hypertrophy of chondrocytes in a tissue sample can be monoclonal or polyclonal. Monoclonal antibody production may be effected by techniques which are well-known in the art. Basically, the process involves first obtaining immune cells (lymphocytes) from the spleen of a mammal (e.g., mouse) which has been previously immunized with the antigen of interest (i.e. the protein or peptide of the present invention) either in vivo or in vitro. The antibody-secreting lymphocytes are then fused with (mouse) myeloma cells or transformed cells, which are capable of replicating indefinitely in cell culture, thereby producing an immortal, immunoglobulin-secreting cell line. The resulting fused cells, or hybridomas, are cultured and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, *Nature* 256:495 (1975), which is hereby incorporated by reference.

Mammalian lymphocytes are immunized by in vivo immunization of the animal (e.g., a mouse) with one of the proteins or polypeptides of the present invention. Such immunizations are repeated as necessary at intervals of up to several weeks to obtain a sufficient titer of antibodies. Appropriate solutions or adjuvants are used as carriers. Following the last antigen boost, the animals are sacrificed and spleen cells removed.

Fusion with mammalian myeloma cells or other fusion partners capable of replicating indefinitely in cell culture is effected by standard and well-known techniques, for example, by using polyethylene glycol (PEG) or other fusing agents (See Milstein and Kohler, *Eur. J. Immunol.* 6:511 (1976), which is hereby incorporated by reference). This immortal cell line, which is preferably murine, but may also be derived from cells of other mammalian species, including but not limited to rats and humans, is selected to be deficient in enzymes necessary for the utilization of certain nutrients, to be capable of rapid growth and to have good fusion capability. Many such cell lines are known to those skilled in the art, and others are regularly described.

Procedures for raising polyclonal antibodies are also well known. Typically, such antibodies can be raised by administering one of the proteins or polypeptides of the present invention subcutaneously to New Zealand white rabbits which have first been bled to obtain pre-immune serum. The antigens can be injected at a total volume of 100 µl per site at six different sites. Each injected material will contain synthetic surfactant adjuvant pluronic polyols, or pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. Ultimately, the rabbits are euthanized with pentobarbitol 150 mg/Kg IV. This and other procedures for raising polyclonal antibodies are disclosed in E. Harlow, et. al., editors, *Antibodies: A Laboratory Manual* (1988), which is hereby incorporated by reference.

In addition to utilizing whole antibodies, the processes of the present invention encompass use of binding portions of such antibodies. Such antibody fragments can be made by conventional procedures, such as proteolytic fragmentation procedures, as described in J. Goding, *Monoclonal Antibodies: Principles and Practice*, pp. 98–118 (New York: Academic Press (1983), which is hereby incorporated by reference.

A variety of different types of assay systems can be used in practicing the method of the present invention. In one embodiment, the assay system has a sandwich or competitive format. Examples of suitable assays include an enzyme-linked immunoadsorbant assay, a radioimmunoassay, a gel diffusion precipitation reaction assay, an immunodiffusion assay, an agglutination assay, a fluorescent immunoassay, a protein A immunoassay, or an immunoelectrophoresis assay.

In an alternative diagnostic embodiment of the present invention, the nucleotide sequences of the isolated DNA molecules of the present invention may be used as a probe in nucleic acid hybridization assays for identifying the occurrence of chondrocytes proliferation or hypertrophy in a tissue sample. The nucleotide sequences of the present invention may be used in any nucleic acid hybridization assay system known in the art, including Southern Blots (Southern, *J. Mol. Biol.,* 98:508 (1975), which is hereby incorporated by reference); Northern Blots (Thomas et al., *Proc. Nat'l Acad. Sci. USA,* 77:5201–05 (1980), which is hereby incorporated by reference); RNAase protection assay systems (Yang et al., *Dev. Biol.,* 135:53–65 (1989) ("Yang"), which is hereby incorporated by reference), and Colony blots (Grunstein et al., *Proc. Nat'l Acad. Sci. USA,* 72:3961–65 (1975), which is hereby incorporated by reference). Alternatively, the isolated DNA molecules of the present invention can be used in a gene amplification detection procedure (e.g., a polymerase chain reaction). See H. A. Erlich et. al., "Recent Advances in the Polymerase Chain Reaction", *Science* 252:1643–51 (1991), which is hereby incorporated by reference.

More generally, the molecular basis suggested herein for the transition of chondrocytes from proliferation to hypertrophy can be used to prevent chondrocytes from transitioning from proliferation to hypertrophy. This transition can be prevented by reducing expression of the protein or polypeptide of the present invention in the chondrocytes, such as, for example, by introducing an antisense or ribozyme construct into the cell. An antisense construct blocks translation of mRNA-encoding the protein or polypeptide of the present invention, thereby reducing expression of the protein. A ribozyme construct cleaves the mRNA encoding the protein or polypeptide of the present invention, thus, also preventing expression of functional protein. In addition, for decreasing in vivo expression of the protein or the polypeptide of the present invention, various gene therapy techniques can also be utilized to introduce the antisense or ribozyme construct into the chondrocytes. Details regarding the introduction of antisense or ribozyme construct into cells for gene therapy can be found in, for example, Christoffersen, *J. Medicinal Chemistry*, 38:2023–2037 (1995), Rossi, *British Medical Bulletin*, 51:217–225 (1995), and Kiehntopf et al., *Lancet*, 345(8956):1027–1031 (1995), which are hereby incorporated by reference.

This technology can also be used to treat a wide variety of diseases caused by undesired chondrocyte proliferation or hypertrophy or undesired chondrocytes transition from proliferation to hypertrophy. For example, by reducing expression of the protein or polypeptide of the present invention in the chondrocytes, arthritic progression of articular chondrocytes can be inhibited. This is achieved by administering to a patient an effective amount of an antibody, binding portion thereof, or probe recognizing proteins or polypeptide selectively expressed in chondrocytes in lower proliferative or upper hypertrophic zones of long bones and embryonic vertebrae growth plates. The antibody, binding portion thereof, or probe can be administered orally, parenterally, for example, subcutaneously, intravenously, intramuscularly, intraperitoneally, by intranasal instillation, or by application to mucous membranes, such as, that of the nose, throat, and bronchial tubes. They may be administered alone or with suitable pharmaceutical carriers, and can be in solid or liquid form such as, tablets, capsules, powders, solutions, suspensions, or emulsions.

The solid unit dosage forms can be of the conventional type. The solid form can be a capsule, such as an ordinary gelatin type containing the antibodies or binding portions thereof of the present invention and a carrier, for example, lubricants and inert fillers, such as lactose, sucrose, or cornstarch. In another embodiment, these compounds are tableted with conventional tablet bases such as lactose, sucrose, or cornstarch, in combination with binders, like acacia, cornstarch, or gelatin, disintegrating agents, such as cornstarch, potato starch, or alginic acid, and a lubricant, like stearic acid or magnesium stearate.

The antibodies or binding portions thereof of this invention can also be administered in injectable dosages by solution or suspension of these materials in a physiologically acceptable diluent with a pharmaceutical carrier. Such carriers include sterile liquids, such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

For use as aerosols, the antibodies or binding portions thereof of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form, such as in a nebulizer or atomizer.

The present invention can also be used for treating bone growth defects, such as non-union bone defects, by increasing expression of a protein or a polypeptide which is expressed selectively in chondrocytes in lower proliferative or upper hypertrophic zones of long bone and embryonic vertebrae growth plates. This can be achieved by administering an effective amount of a protein or polypeptide of the present invention to the patient suffering one or more of these conditions. Alternatively, these conditions can be treated by administering an effective amount of an expression system comprising a DNA molecule encoding a protein or polypeptide of the present invention to the patient. The proteins and expression systems used to treat these bone growth defects can be administered by the routes and in the forms discussed above with respect to administration of antibodies.

The biological role of the protein, though not known for certain, is believed to be that of a phosphatase, although the disclosure of this biological role is not intended to be in any way limiting and should not be construed as a limitation on the uses to which this protein may be put. In view of the potential phosphatase activity, specific inhibitors or activators of this putative phosphatase can be used to treat the diseases outlined above.

The following examples are provided to illustrate embodiments of the present invention but are by no means intended to limit its scope.

EXAMPLES

Example 1

Materials and Methods

Growth Plate and Articular Chondrocyte Isolation.

Chondrocytes were isolated as described in O'Keefe et al., *J. Bone and Joint Surg.*, 71A:607–620 (1989), which is hereby incorporated by reference. Briefly, 3 to 5 week old chicks were sacrificed in a $CO_2$ canister, and the long bones of the legs dissected free of soft tissue. Cartilaginous tissue from both the proximal and distal growth plates of both long bones of each leg, or of the knee joint articular surfaces, were dissected and placed in modified F-12 medium (magnesium-free, 0.5 mM $CaCl_2$, penicillin 100 units/ml, streptomycin 100 mg/ml) and sequentially digested with trypsin, hyaluronidase, and collagenase as described. The washed cells were either extracted directly for RNA or plated at subconfluent density in Dulbecco's Minimal Essential Medium ("DMEM") with 5% fetal bovine serum.

Sternal Chondrocyte Isolation.

Cranial and caudal sternal chondrocytes were isolated and cultured as described in Leboy, which is hereby incorporated by reference. Cells were released from the cranial and caudal thirds of embryonic day 14 chick sterna by trypsin digestion and cultured under standard conditions for 5 days. At the end of this primary culture period, the floating cell population was greater than 95% chondrocytic and was placed in secondary culture with DMEM plus 10% NuSerum (Sullivan, which is hereby incorporated by reference.) For culture under serum-free conditions, the secondary cultures were switched after 24 hours to DMEM supplemented with 60 ng/ml insulin and 10 pM tri-iodothyronine (Bohme et al., *J. Cell Biol.*, 116:1035–42 (1992), which is hereby incorporated by reference). The ascorbate concentration in test cultures was increased gradually to prevent dedifferentiation of the cells.

RNA Isolation.

RNA was purified by extraction with RNAzol B (Tel-Test, Inc.) according to the manufacturer's directions. Uncultured chondrocytes were collected by centrifugation (1500 g, 5 min), washed in phosphate-buffered saline ("PBS"), and respun. RNAzol B was added to the cell pellet in the amount of 0.2 ml per $10^6$ cells and immediately mixed by vortexing. Cultured chondrocytes were washed twice with cold PBS, then extracted with 2.5 ml RNAzol B per 100 mm dish by passage through a pipette. Yields of RNA were approximately 5 μg total RNA per million growth plate chondrocytes, 2–3 μg RNA per million articular chondrocytes, and 20 μg RNA per million sternal chondrocytes. Fresh growth plate tissue was frozen and then pulverized with a mortar and pestle in liquid nitrogen. The pulverized tissue was then extracted by mincing with a Polytron in RNAzol on ice. Poly A+ RNA was prepared by two consecutive passes of the RNA over an oligo dT-cellulose column as described in Maniatis et al., *Molecular Cloning: A Laboratory Manual*, New York: Cold Spring Harbor Press, (1982) ("Maniatis"), which is hereby incorporated by reference), reextracted with organic solvents, and precipitated with ethanol.

RNA Blot Analysis.

RNA analysis on Northern Blots was performed using morpholinepropanesulfonic acid ("MOPS") (200 mM MOPS, 50 mM NaOAc, 10 mM EDTA, pH 7.0)-buffered formaldehyde (2.2 M) agarose gels as described in Maniatis, which is hereby incorporated by reference. 5–10 μg of total RNA or 0.5 μg of polyA+ RNA was denatured in formamide/formaldehyde and electrophoresed. The gel was stained with 0.25 μg/ml Ethidium bromide for 5 minutes, destained for 1 hr with several changes of distilled water, and photographed, and the RNA was transferred to Gene Screen Plus (DuPont- NEN, Boston, Mass.) using an overnight capillary transfer with 10xSSC. rRNA bands and size standards were visualized on the paper (via Ethidium Bromide staining), and their locations were marked for reference after autoradiography.

RNA blots were stripped according the manufacturer's instructions (DuPont- NEN, Boston, Mass.). Chicken glyceraldehyde-3-phosphate dehydrogenase ("GAPDH") was used as a probe to standardize loading for Northern and RNAase protection analyses. The chicken GAPDH was cloned out of the growth plate cDNA library using the rat GAPDH fragment (Ambion) as a probe. The chicken GAPDH sequence used as a probe corresponds to nucleotides 265–533 of the rat GAPDH cDNA (Genbank accession number M17701). For the experiment in FIG. 4, a 1.45 kb human β-actin cDNA was used as control (Gunning et al., *Mol. Cell Biol.*, 3:787–795 (1983), which is hereby incorporated by reference).

RNAase protection assays.

DNA fragments that served as templates for riboprobe production were cloned into either the SK⁻ or SK⁺ Bluescript vectors (Stratagene). RNA probes were synthesized to a specific activity of $1 \times 10^8$ dpm/μg in the presence of (alpha-$^{32}$P) uridine triphosphate ("UTP") using T7 or T3 RNA polymerase (Yang, which is hereby incorporated by reference).

Growth plate or articular chondrocyte RNA and yeast tRNA were hybridized with an excess of the $^{32}$P-labeled probe (300 pg) in a volume of 20 μl at 50° C. in 50% formamide/40 mM 1,4-piperazinebis(ethane-sulfonic acid ("PIPES"), pH 6.7/0.5 M NaCl/1 mM EDTA for 16–20 hours. The RNA:RNA hybrids were treated with RNAases A and T1, extracted with phenol/chloroform, precipitated, and then collected by centrifugation. Protected RNA fragments were separated on 4 or 5% polyacrylamide gels, then displayed by autoradiography.

Differential display of growth plate and articular chondrocyte gene expression.

Following the original protocol described in Liang et al., *Science*, 257:967–971 (1992) ("Liang"), which is hereby incorporated by reference), polyA⁺RNA from articular and growth plate chondrocytes was collected and validated by Northern Blot hybridization to type II and type X collagen probes. 0.5 μg polyA⁺ RNA was reverse transcribed using Superscript reverse transcriptase (Gibco/BRL), and 2.5 μM $T_{11}$CA as a primer, in a volume of 20 μl. Two μl of the cDNA was then amplified using 2.5 units of Taq polymerase (Promega) with 20 μM dNTP and 0.5 μM (alpha-$^{35}$S) dATP in a volume of 20 μl. The PCR conditions were: 1) 94° C. for 30 sec, 42° C. for 1 min, 72° C. for 30 sec for 40 cycles and 2) 94° C. for 30 sec, 42° C. for 1 min, 72° C. for 5 min for 1 cycle. Two μl of this RT-PCR mix was electrophoresed on a 6% denaturing acrylamide gel, and the amplified bands were displayed by autoradiography of the dried gel.

The differentially amplified Band 17 was recovered by a method suggested by P. Liang. The area of the gel that corresponded to the differentially expressed band was excised with a scalpel, placed into 200 μl water for 15 min at 22° C., then incubated at 100° C. for 15 min. After microfuging 10 minutes, the supernatant was transferred to another tube, glycogen was added to 400 μg/ml, sodium acetate to 0.3M, and 3 volumes of ethanol was used to precipitate the DNA overnight at −70° C. The primary amplified bands were recovered by centrifugation. The dried DNA pellet was resuspended in 15 μl 10 mM Tris-1 mM EDTA (TE).

Reamplification of the differentially expressed cDNA was performed with primers that had restriction sites added to the original $T_{11}$CA (SEQ. ID. No. 15) and 10-mer oligonucleotides. The original 3' end primer was 5'-$T_{11}$CA-3' (SEQ. ID. No. 15); the primer for reamplification was 5'-CCGCGGATCCT$_{11}$CA-3' (SEQ. ID. No. 16), thus inserting a BamHI site in the amplified fragment. The original 5' end primer was 5'-CTTGATTGCC-3' (SEQ. ID. No. 17); the primer for reamplification was 5'-CCGCGAATTCCTTGATTGCC-3' (SEQ. ID. No. 18), thus inserting an EcoRI site at the other side of the amplified fragment. The yield from the second amplification is 150 to 300 ng DNA. The added restriction sites facilitated cloning into phagemid and M13 vectors, which was done by standard protocols (Ausubel et al., *Current Protocols in Molecular Biology*, New York: John Wiley and Sons (1987) ("Ausubel"), which is hereby incorporated by reference).

In Situ Hybridization.

Sections were treated with a modification of the protocol described in Angerer et al., "In Situ Hybridization with RNA Probes: An Annotated Recipe," in *In Situ Hybridization: Applications to Neurobiology*, Valentino, ed., New York: Oxford University Press, pp. 42–70 (1987), which is hereby incorporated by reference. Tissue sections were treated for 30 min at 37° C. with 1 μg/ml proteinase K, washed and dipped in fresh 0.25% acetic anhydride in 0.1 M triethanolamine (pH 8.0) for 10 min. After dehydration through a series of ethanol washes, the sections were dried and hybridized overnight at 56° C. in 50% formamide, 0.3 M NaCl, 10 mM Tris-Cl (pH 8.0), 1 mM EDTA, 1x Denhardts solution, 10% Dextran sulfate, 0.5 mg/ml yeast tRNA, and 0.3 μg/ml probe. Riboprobes were generated as above.

The slides were washed twice in a solution containing 0.15 M NaCl, 0.015 M trisodium citrate ("1xSSC") for 10 min and once for 40 min. Slides were treated with RNAase A (20 μg/ml in RNAase buffer (0.5 M NaCl, 10 mM Tris-Cl and 1 mM EDTA, pH 7.5) for 30 min. at 37° C., then passed through 30 minute washes of RNase buffer at 37° C., 0.1×SSC at room temperature, 0.1×SSC at 68° C., and 0.1×SSC at room temperature. The slides were dehydrated, dried, and coated with nitroblue tetrazolium ("NBT2") emulsion for autoradiography. Exposure times were 17 days. Slides were developed, counterstained with hematoxylin and eosin, and coverslipped with an organic solvent-based mounting solution, such as Permount.

cDNA and genomic library screening.

Double stranded DNA fragments were labeled with (alpha-$^{32}$P-) dCTP (New England Nuclear) using the Megaprime random priming kit from Amersham according to the manufacturer's directions. Specific activities of the various probes were 1.0 to 6.0×10$^8$ cpm/μg. These probes were used for hybridization to Northern Blots, Southern Blots, and cDNA library filters, at a concentration of 0.5 to 1×10$^6$ cpm/ml hybridization solution.

Two chicken growth plate cDNA libraries and one chicken genomic library were used for obtaining Band 17 sequences. In a typical screening, a library was plated at 30,000 plaques per 150 mm petri plate. Phage DNA was immobilized on Colony Plaque Screen (Dupont-NEN, Boston, Mass.) and probed according to the manufacturers' instructions. Two filters were used per plate. Prehybridization was performed for 1–3 hours in 5 ml of prehybridization buffer per filter (6×SSC, 1% SDS, 5×Denhardt's solution, 10% Dextran sulfate, and 100 μg/ml denatured salmon sperm DNA). Denatured, random-primed probe was added and the filters were hybridized 16–20 hours at 60° C. The final wash was in 0.1×SSC, 0.1% SDS at 60° C. Autoradiography was carried out for 1–3 days at −70° C. using two intensifying screens.

Plaques hybridizing to the probe were purified through more rounds of screening. Phagemid cDNA was "Zapped" out employing an M13 helper phage R408 (Stratagene) according to the manufacturer's instructions. Phagemids harboring the largest overlapping inserts were selected for sequence analysis. Genomic DNA was recovered by preparation of lambda DNA (Ausubel, which is hereby incorporated by reference) and subsequent subcloning into the SK-vector.

Sequence analysis.

Sequence analysis was performed by the chain termination method described in Sanger, *Proc. Nat. Acad. Sci. USA*, 74:5463–5467 (1977), which is hereby incorporated by reference, as modified in Biggin et al., *Proc. Nat. Acad. Sci. USA*, 80:3963–3965 (1983), which is hereby incorporated by reference, for use with the (alpha-$^{35}$S-) dATP and T7 polymerase (Sequenase from U.S. Biochemical). Sequences were read and recorded manually, then entered into a VAX computer and analyzed using the GCG programs (*Program Manual for the Wisconsin Package,* Wisconsin: Genetics Computer Group, (1994), which is hereby incorporated by reference). Comparison of Band 17 sequence with the national data bank used the BLAST search program disclosed in Altschul et al., *J. Mol. Biol.,* 215:403–410 (1990), which is hereby incorporated by reference.

Example 2

Identification of Band 17

Figure 1B:
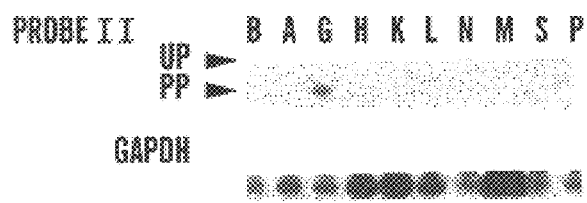
FIGS. 1B and 1C are RNAase protection analyses.

The differential display technique described in Liang, which is hereby incorporated by reference, was used to amplify cDNAs from growth plate and articular chondrocytes from juvenile chicks. PolyA$^+$RNAs were prepared from enzymatically released growth plate and epiphyseal chondrocytes and were used as a templates for reverse transcription and subsequent PCR. Band 17 was originally amplified as a 260 nucleotide cDNA that was displayed only in PCR products from growth plate chondrocytes. The cDNA was reamplified and cloned into Stratagene vector SK$^-$ to facilitate further analysis. The 260 bp Band 17 cDNA detected two transcripts of 2.2 and 5.0 kb on Northern Blots of growth plate RNA (FIG. 1A, probe II, Lane G). Neither transcript was detectable on Northern Blots of articular chondrocyte RNA (FIG. 1A, probe II, Lane A). RNAase protection using the 260 nt RNA antisense probe confirmed that Band 17 is strongly expressed in growth plate chondrocytes (FIG. 1B, lane G) and undetectable in articular chondrocytes (FIG. 1B, lane A).

Example 3

Band 17 Transcripts

As the cloning of Band 17 cDNA proceeded, additional transcripts of 6.2 kb and 1.7 kb were detected by Northern Blot hybridization of cDNA probes from the 5' end of Band 17 (FIG. 1A, probe I). The 6.2 kb transcript is significantly greater in abundance than the 5.0, 2.2, and 1.7 kb transcripts and is the result of alternative splicing (see below, and FIG. 5 for location of probes and splice site). cDNA probes from the 5' side of the alternative splice site detect the 6.2, 5.0, 2.2, and 1.7 kb transcripts (e.g., probe I in FIG. 1A). Probes from the alternative 3' ends of Band 17 detect either the 5.0 and 2.2 kb transcripts (FIG. 1A, probe II), the 6.2 kb (FIG. 1A, probe IV), or the 5.0 kb transcript. None of the Band 17 transcripts are detectable in articular chondrocyte RNA (FIG. 1A, Lanes A). The 1.7 kb transcript was only detected by cDNA probes from the 5' side of the splice site, and may include additional 5' and/or 3' exons not yet cloned.

Figure 1C:
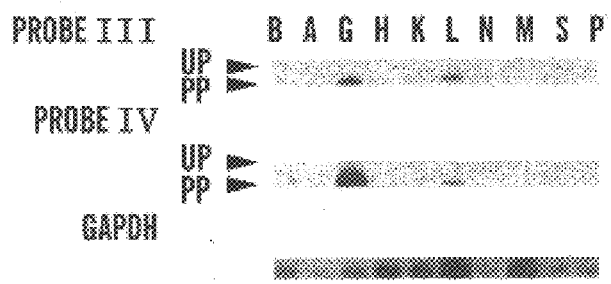

RNAase protection demonstrates that the 6.2, 5.0, and 2.2 kb Band 17 transcripts show the same specificity for the growth plate (FIGS. 1B and 1C). The RNAase protections were performed with cRNAs that detect either the 2.2 and 5.0 kb transcripts (probe II), the 5.0 transcript (probe III), or the 6.2 kb transcript (probe IV). Compared to expression in the growth plate, Band 17 is weakly expressed in kidney (K), liver (L), lung (N), skin (S), and spleen (P). Expression was not detected in brain (B), articular chondrocytes (A), heart (H), and muscle (M).

Example 4

Band 17 Localization

In situ hybridization demonstrated that Band 17 message is restricted to the lower proliferative/upper hypertrophic region of the juvenile growth plate (FIG. 2, A–D). A similar pattern of expression for Band 17 was seen in embryonic vertebrae, in which Band 17 is expressed at the border of proliferating and hypertrophic cells (FIG. 2, E, F). In contrast to the expression of type X collagen (Oshima; Leboy et al., *J. Biol. Chem.,* 263:8515–8520 (1988); and Luvalle et al., *Dev. Biol.,* 133:613–616 (1989), which are hereby incorporated by reference), Band 17 expression is not found throughout the hypertrophic zone. Band 17 was not detected elsewhere in the embryo, including developing limbs that had no hypertrophic cells. This suggests not only that Band 17 is expressed specifically in chondrocytes destined for mineralization (FIG. 1) but also that Band 17 is expressed in a spatially limited region where chondrocytes are exiting the cell cycle and beginning hypertrophic differentiation (FIG. 2). The role for Band 17 in the transition from proliferation to differentiation has been corroborated through the use of two chondrocyte culture model systems.

Example 5

Temporal Expression of Band 17

Cultured upper sternal chondrocytes from late chick embryos have been widely used as an in vitro model of chondrocyte differentiation. Ascorbate treatment of cultured sternal chondrocytes results in steady increase of type X collagen and alkaline phosphatase, eventually leading to calcification of the matrix. Type X mRNA and alkaline phosphatase activity both increase approximately 14 fold over nontreated controls during a 7 day period. Concomitantly, collagen types II and IX decrease gradually, showing a greater rate of decrease in cells treated with ascorbate (Leboy, which is hereby incorporated by reference). Ascorbate induces the hypertrophic phenotype in these cells in a manner independent of ascorbate's effect on collagen processing (Sullivan, which is hereby incorporated by reference). Ascorbate induced Band 17 mRNA at least 5 fold over a 2–3 day period (FIG. 3) in chondrocytes cultured either with (lanes 3 and 4) or without (lanes 1 and 2) serum. The increase in Band 17 message during short term culture suggests, as does the in situ hybridization data, that Band 17 functions during the initial stages of hypertrophy as opposed to the later mineralization state. Band 17 mRNA appeared to be induced slightly more than type X message over the same duration (Leboy, which is hereby incorporated by reference), suggesting that Band 17 expression is initiated no later than the initiation of type X synthesis.

Band 17 expression was also examined in monolayer cultures of juvenile (3 to 5 week old) chick chondrocytes, cells that are more differentiated than those found in embryonic chick sternum. Monolayer cultures of growth plate chondrocytes derived from juvenile chickens showed rapid increases in Type X collagen message and protein in the 24 hours after plating. This effect was seen in cells derived from all zones of the growth plate, indicating that cells not normally expressing hypertrophic marker genes do so upon release from their matrix (O'Keefe et al., *J. Bone Mineral Res.*, 9:1713–1518 (1994) ("O'Keefe"), which is hereby incorporated by reference). Band 17 expression increases during enzymatic release from the matrix (FIG. 4A). However, Band 17 expression decreased significantly during the first 24 hours of growth in culture, in contrast to type X expression (O'Keefe, which is hereby incorporated by reference). Furthermore, Band 17 expression remained at low levels (FIG. 4B). During this same period, type X collagen remained elevated and constant, and type II collagen decreased (FIG. 4C). In a separate experiment using identical isolation and culturing conditions, alkaline phosphatase activity was shown to increase, then remain steady, while cellular proliferation decreased. Thus, many parameters of the hypertrophic phenotype are consistently found in these cells throughout the culture period while Band 17 expression is found only in the initial stages of culturing.

In summary, four independent aspects of Band 17 gene expression support the hypothesis that Band 17 is involved in the commitment of proliferating chondrocytes to hypertrophy. Band 17 expression: 1) is specific to growth plate chondrocytes; 2) is restricted to the lower proliferative/upper hypertrophic zone of the growth plate; 3) is increased concomitantly with induction of hypertrophy in vitro; and 4) is independently regulated compared to hypertrophic marker genes. This pattern of expression places Band 17 in a limited group of genes that are expressed differentially within the growth plate.

Example 6

Alternative Splicing of Band 17

FIG. 5 summarizes the known intron/exon structure of the Band 17 locus compiled from four sets of data: 1) probing RNA blots with Band 17 cDNAs (as detailed above), 2) probing a genomic Southern Blots with Band 17 cDNAs, 3) cloning and sequence analysis of overlapping cDNAs and 4) cloning and sequence analysis of a 12.5 kb genomic fragment.

The splice sites have been identified by comparison of Band 17 cDNAs with genomic DNA sequence. The 2.2, 5.0, and 6.2 kb transcripts share at least three exons at the 5' end of the mRNA, but the 6.2 kb transcript diverges from the 2.2 and 5.0 kb transcripts beyond the 3' end of exon C. The 5.0 and 2.2 kb transcripts have approximately 1 kb of common sequence at the 5' end of exon D. The 3' end of 2.2 kb transcript is approximately at the NcoI site in exon D (FIG. 5), as cDNAs from exon D 3' to that site do not detect the shorter transcript. This results in exon D-short ($D_s$, FIG. 5). The remainder of exon D is approximately 3 kb long and contains no open reading frames. The 3' end of exon D has been approximately mapped by an AATAAA consensus termination sequence and by genomic DNA fragments downstream of this site that do not detect the 5.0 kb transcript.

Figure 6:
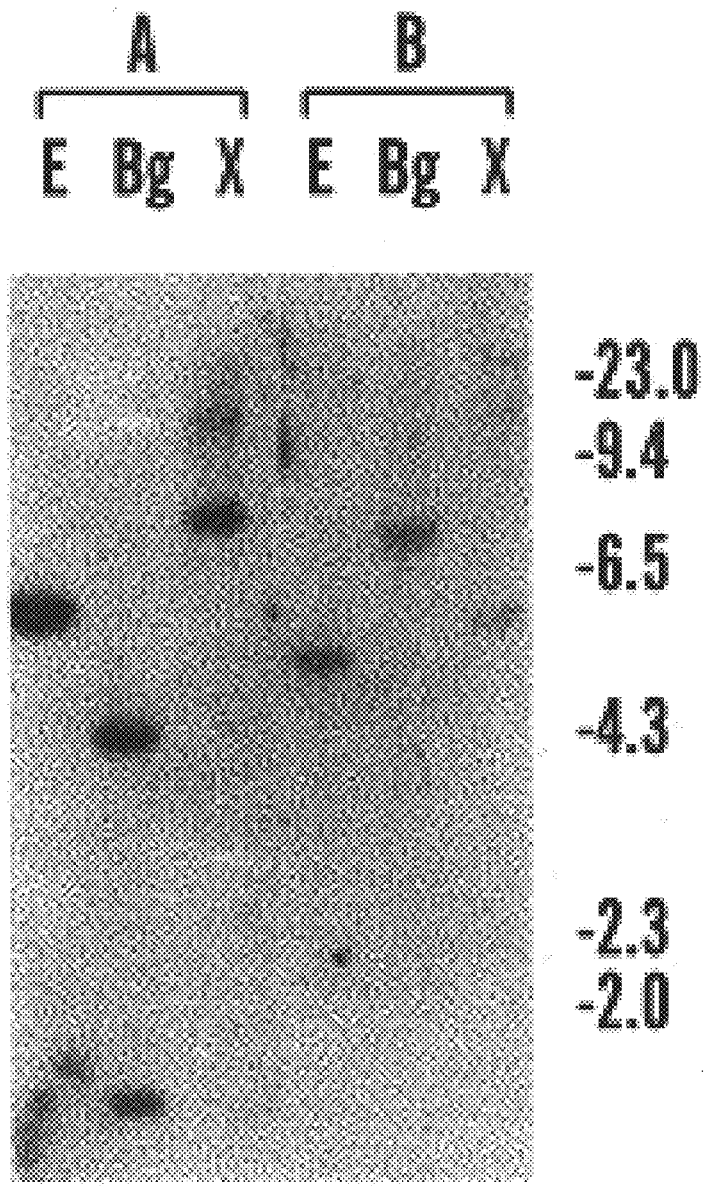
FIGS. 6A and 6B are genomic Southern Blots. Ten µg genomic DNA was digested with either EcoRI (E), BglII (Bg), or XbaI (X) and the digested fragments were separated on a 1% agarose gel. The DNA was blotted to GeneScreen Plus, then hybridized to a random primed probe.

The multiple transcripts detected with the Band 17 cDNA probes could arise from duplicated, highly similar genes. This possibility was investigated by probing a genomic Southern Blot with a cDNA that spans a Bgl II site within exon D (FIG. 6, probe V). Sequence and restriction analysis of cloned genomic DNA predicts that probe V should detect Bgl II fragments of 1.7 and 3.8 kb, and single EcoRI and Xba I fragments of 5.3 and 8.0 kb. FIG. 6 demonstrates that these fragments are the only ones detected by probe I. Similarly, probe IV, which is specific for the 6.2 kb transcript, also detects single EcoRI, Bgl II, and Xba I fragments on a genomic Southern (FIG. 6) that are distinct from those spanning exons B–D.

Analysis of Band 17 cDNAs provides corroboration that the three Band 17 transcripts are derived from single gene. Multiple cDNA sequences that diverge at the splice point between the 2.2 and 5.0 transcripts (exons C/D), and 6.2 kb transcript (exons C/E) have been obtained. Sequence analyses of the independent cDNAs representing the three transcripts do not indicate variability that would suggest an additional gene as a source for one of the fragments. The 2.2 and 5.0 kb cDNAs overlap for approximately the first 1000 bp of the exon D (FIG. 5), and the 2.2, 5.0, and 6.2 kb transcripts overlap for all of the exons 5' to the alternative splice site, which is at least 600 bp. Were the different transcripts arising from a second locus, perfect homology would be highly unlikely.

Example 7

Proteins Encoded by Band 17

FIG. 7 displays the Band 17 cDNA with the predicted translation of the only significant open reading frame in the cDNA sequence. The predicted amino acid sequence is for the cDNA that corresponds to the 6.2 kb mRNA. The alternative splice site for the 6.2 and 5.0 kb transcripts is at position 587. In the 2.2 and 5.0 kb transcripts the sequence added by exon D begins 5'-TTGA-3', the last three nucleotides encoding a termination codon. Thus, the protein translated from the 2.2 and 5.0 kb transcripts is predicted to be 131 amino acids shorter at the C-terminal than the protein from the 6.2 kb transcript.

The program MOTIFS of the Wisconsin Computer group sequence analysis software matched the C-terminal of the longer protein, Ala-Asp-Glu-Leu-COOH (SEQ. ID. No. 13), to a putative consensus sequence that targets and retains proteins to the luminal space of the endoplasmic reticulum (Munro et al., *Cell,* 48:899–907 (1987), which is hereby incorporated by reference). A number of different luminal proteins in vertebrates end in the similar Lys/His-Asp-Glu-Leu (SEQ. ID. No. 14). The initial basic residue of this signalling tetrapeptide sequence is conserved in vertebrates, but an alanine at the N-terminal position can be found in a yeast protein. Furthermore, a number of luminal proteins, such as rat, chick, and human protein disulphide isomerase (Edman et al., *Nature,* 317:267–270 (1985); Geetha-Habib et al., *Cell,* 54:1053–1060 (1988); and Cheng et al., *J. Biol. Chem.,* 262:11221–11227 (1987), which are hereby incorporated by reference), chick and mouse Hsp47 (Hirayoshi et al., *Mol. Cell. Biol.,* 11:4036–4044 (1991) and Takechi et al., *Eur. J. Biochem.,* 206:323–329 (1992), which are hereby incorporated by reference) and chick GRP94 (Kulomaa et al., *Biochemistry,* 25:6244–6251 (1986), which is hereby incorporated by reference), have a bulky hydrophobic group as methionine or valine preceding the lysine, as does Band 17.

Example 8

Band 17 Homology with a Human cDNA

Comparison of the Band 17 sequence with NCBI data bands detected homology with two overlapping uncharacterized cDNA clones from infant human brain tissue (FIG. 8A). This homology is found within the protein coding sequence of Band 17 (FIG. 8B) and extends into the sequences specific to the 6.2 kb cDNA. Translation of the two sequence predicts a high level of homology (70% identity) between the human and chicken genes. As yet there are no other significant homologies between these two sequences and any other nucleotide or amino acid sequences in the data banks. However, the tight conservation between the chicken and human primary structure suggests that the function of the two proteins has been conserved.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. An isolated DNA molecule encoding a protein or polypeptide selectively expressed in chondrocytes in lower proliferative or upper hypertrophic zones of long bone and embryonic vertebrae growth plates, wherein the protein or polypeptide comprises an amino acid sequence consisting of SEQ. ID. No. 3.

2. An isolated DNA molecule according to claim 1, wherein said DNA molecule comprises a nucleotide sequence consisting of SEQ. ID. No. 2.

3. An isolated DNA molecule according to claim 1, wherein said DNA molecule comprises a nucleotide sequence consisting of SEQ. ID. No. 4.

4. An isolated DNA molecule according to claim 1, wherein said DNA molecule comprises a nucleotide sequence consisting of SEQ. ID. No. 5.

5. A vector or recombinant plasmid comprising a DNA molecule according to claim 1.

6. A vector or recombinant plasmid according to claim 5, wherein said DNA molecule comprises a nucleotide sequence consisting of SEQ. ID. No. 2, SEQ. ID. No. 4, or SEQ. ID. No. 5.

7. A host cell transformed with a DNA molecule according to claim 1, wherein said DNA molecule is heterologous to said host cell.

8. A host cell according to claim 7, wherein said DNA molecule comprises a nucleotide sequence consisting of SEQ. ID. No. 2, SEQ. ID. No. 4, or SEQ. ID. No. 5.

9. An isolated DNA molecule encoding a protein or polypeptide selectively expressed in chondrocytes in lower proliferative or upper hypertrophic zones of long bone and embryonic vertebrae growth plates, wherein the protein or polypeptide comprises an amino acid sequence consisting of SEQ. ID. No. 7.

10. An isolated DNA molecule according to claim 9, wherein said DNA molecule comprises a nucleotide sequence consisting of SEQ. ID. No. 6.

11. An isolated DNA molecule according to claim 9, wherein said DNA molecule comprises a nucleotide sequence consisting of SEQ. ID. No. 8.

12. A vector or recombinant plasmid comprising a DNA molecule according to claim 9.

13. A vector or recombinant plasmid according to claim 12, wherein said DNA molecule comprises a nucleotide sequence consisting of SEQ. ID. No. 6 or SEQ. ID. No. 8.

14. A host cell transformed with a DNA molecule according to claim 9, wherein said DNA molecule is heterologous to said host cell.

15. A host cell according to claim 14, wherein said DNA molecule comprises a nucleotide sequence consisting of SEQ. ID. No. 6 or SEQ. ID. No. 8.

16. An isolated DNA molecule encoding a polypeptide comprising an amino acid sequence consisting of SEQ. ID. No. 11.

17. An isolated DNA molecule encoding a polypeptide comprising an amino acid sequence consisting of SEQ. ID. No. 12.

* * * * *

SEQUENCE LISTING

<160> NUMBER OF SEQ ID NOS: 18

<210> SEQ ID NO 1
<211> LENGTH: 8321
<212> TYPE: DNA
<213> ORGANISM: Gallus gallus

<400> SEQUENCE: 1

```
gatcactgcg acaagttcgt ggccttcgtg gaggacaacg acacagccat gtaccaagtg      60
aacgccttca aagagggccc ggagatgagg aaggtgttgg agaaggtggc gagtgccctg     120
tgtctgccgg ccagcgagct gaacgcaggt aacagagcgg ccccgggtac gctgcgctca     180
gtgtgatgcg ggatgtgctg cagttatgca gagttcctgt ctaaaataca agctgaacca     240
gatgcagtca tgcagggttc gtgtggggct gcagtagtgc gtgcttgtta gtcaacagaa     300
agaaaacacc tttgggagta tctttcttgg agacgagtgg aagtatcagc tgtacctttg     360
ttttaagggc tcagctttac ttttgctttg agttatgagt gtgttacctt ttaattctcc     420
ttctgtaaaa tgttgcaatt caagcatgca gatagttgaa gggaagggag gatgtgtctg     480
cgttgtacct tcgcttgtct acagggagca catttcccat gctcaggaag cccccagaaa     540
taagcactgc tgtcatttcc agcattcccc caaagatgtg atcctaaaac cacgtcacgc     600
tgcagctcaa acccagccag cagcatacag gttaagcatg gcagcctgag actgctccac     660
agtgagccgg cacgcctcca cctgcccctc ttctgccttt tgtgatagta aggctatccc     720
agcagtggga ctatcacagg tgcatcagtt cagtgtggaa tgtgtggttt tgtttccctg     780
aggtttgcat tctgcacgat aactctattg gaaactttgt tgcttggcat ttgggctggt     840
gattgttttc aaccctaaat tgtagttact cgtacaaaac catgacaagg ggaaagttgg     900
gagaaagttg ctagttctgt ggtggtggtt ttatcccttg ctcctttctt ggatctattg     960
cagatctcgt tcaagtggct ttcctcactt gctcgtatga gttggctata aaaaatgtga    1020
cctccccgtg gtgttcgctc ttcagtgaag aagatgctaa ggtaggtgct aaatgcagag    1080
ggcagagaga tttgagaagc cttcaaaaca tgcctcactg tttggatgtt gttttgtggg    1140
cagttgtaag ttctgtgccc gtccttcttc aaccttcatt aggtttggtg ctccattagc    1200
gctgcattgg tctccaaaga gctgtggggtt aatcaagcag taggactgaa ataccttctg    1260
```

```
cattcagact taaatattgg cagtgtctta atttgtcctg actaaaatga tcttttccat    1320
tgcacactta attcatgtaa tgctttttc tttctgtaac acctgaaatg ctctggacaa     1380
ctttgtttta catgtattat ttttatatga taaaatgtct tgattttaga ggacagcaaa    1440
taaggtcttt taggtcctct gtgacttctt ttctgaggcc caactggtct ctaattcctg    1500
ttaataaaac tagtagaacc tggataaata tgacttgctt tggattactc tttggaggga    1560
ttgagagatt tggggattaa gaatgatgcc atttatttgg cactgcaaaa cacgtttagc    1620
aatgcccctg cagaggctcc taaggaagc ttagcagccc tgccaaagag aaaaaccctg     1680
gagtcaggag gaagcggtct cctctcaaag aagaggaggg tcagcaggaa tttgtgctgt    1740
ttccttctaa tagcttagtg agagaggaaa gcttgctgat taagcggtta cttggcacgt    1800
taagaatatg gggtgtttga gcagctctgc tggaagactc tacaaggttg aattgcccag    1860
cagtgcagtg gcagttggtg ttcagtgtga aattacgtgc atggagtaag aggttaaagc    1920
tccatcagtg aggtggtggg ctctcagatc ccttttatt atttatttat ttattttcac    1980
tgtatgcaat agtaaaaact tgtaaactgt gttaacttta ggtactggag tacctgaatg    2040
acctgaagca atactggaag agaggatatg gctatgacat caatagtcgc tccagctgca    2100
ttttattcca ggatatcttc cagcagttgg acaaagcagt ggatgagagc agaaggtaaa    2160
ttaaaaaaaa aaaagggggg ggggggggg gaagcttttg tgttgactga ctgcaagctt     2220
tctgtggtta atcctgagtt ggatttgagt agcagttaaa cacttcagac acaagaatgc    2280
taggagaagt ttggttagga gaacttgtga ttagagagaa caaaatcctt aataggatcg    2340
ttactgtaga gtgcaaatag gcttgaggtt ttattttcc cattgatgct tttgtgccca     2400
gtggatttat ttccatcttt taacttactg atctgcacag gccttcaaag gacagccagt    2460
tactgtgtct gacagtggtg gttttttcct gctgaacaat gaattttttg tttaaaatgt    2520 cttgttaaa aagcatttgt ggtgaaagtg gaaggctgt aggttaaaaa agcaatatg       2580 atcgattctg ctttctggtt acttaaacac ttcagcatga aagtcttgtt ttctttccat    2640
gtgtgtttga catctcttgc actattaaag ctttctgagc tttaaagctt caggctgaag    2700
gtgctgaaat gcaattacaa aagaataatt atttcaagtg aatccaaaca ctcagtgacc    2760
ctagatgaga actgcctgtt gcagaatcca ccaagcctga actgtaacag caaaccagcc    2820
ttgtcatgcc tgcttctttg taactgcaga aagacaaact taggcagtat actcggtccc    2880
tgcacaaaca ggagaaaggt acttgagccc tgaggctgtt gtaaaagcct tggtttgttg    2940
tacgaacatg aggccagtaa tttagccagc cagccactct cttagatatt tactttcgca    3000
tccttactca tctgcagcaa aactgcccat tgggagcaat gctgtaggtg taggaagttg    3060
ttagacctca catgtatctg ttagcagaca caaagatagc acaagcaaga gtctgcagag    3120
gagggtggtc tgatgaagtg gtttgtgttc agctagttcc atggtttggc aagtcatttt    3180
gtgtcagaga aggaagaaca gcagtggtac tccttccagg aactcttaca gccctcaaaa    3240
ttgcctttaa cgtgccttgg aggtacctat gcttccttaa aagctaaaga caagatgcct    3300
gtgttcttgt gtgtattgtt tactcctatc agctgctatc agtcggcagc ggtgatctgt    3360
tgtaacctag agaaacagt atagaaaaca aaggctttag ttacaggttt gggtgtttat     3420
gtcacaagat tagctgtatt tgctttcatg tgccagtaat aaaatttttg agagctgcgt    3480
taggcttaaa aacagtgcat gcatatggga ataatttaca acctgcatga atgttgtttt    3540
tctaacagag gaattacaaa ttcatagctt agtgatcagc catgtgaatc agtacctgag    3600
caggtaagcg cacaaatgtt tacaaaagca cacaaaatca aggaggtgat aacaagattg    3660
```

-continued

```
tgtaaacatt gtgcctttaa atggttcgtt ggaatcaatg tatgagtagc gtaaggtgac    3720
caagttcagc tttgatattg atatagaaaa agtagttgta tgtgatgggt gtacttacat    3780
tgctagcatc cttggggttc tagttctaaa tttagggtac tgaagtaggt caaaaattat    3840
ttagtgtttc aggaacgaaa gctgaagtca ctgatacttg aagctatatg tgtgtatttt    3900
tttttacttg ataacatgta agaaagcact ttattttccc ctgtcagttg acagattgaa    3960
aatagaggta gccttgcaat tttggatcag aggaatgatc tatcaaattg tgaagtcttc    4020
ctccttggaa gaaaagcttc aaaagctgcc ctggcactac cctgggatac agcctccaga    4080
ggtcccttcc cacctcaagc attctgtaac gccaatcact tcttacaaag gagactgcga    4140
agaagttgtt catctagatt tttgctcact gaggatctga gttaaatatc aacagtgata    4200
gaactgactg ttaagtcagt tgaagcagaa ttctcagtca gttggctttt ttgttgtgct    4260
tcagtgctgg atgcagagat gctgtgtgtt aagccctctt cattttgcta tgaacaggct    4320
agaacttgtt gtaagctagt tgtaagcatg aaaccaacat agcaccgagg actaattgtg    4380
aaggaaaggt gggcagaagg aagtggctgt tgatagcaaa ctctctgcag caagcctgga    4440
cattgtgctg ctaaatcatt ctggtttttg gaaatctaag ggctgtcaga gctgttgatc    4500
cctctcattt tgagagtggt ggagtcaaag ctgtggttat gctagattgc cctttaaata    4560
aatctctact gtatcctttc ttcagcattc tgggaagcta ataaaaaat gcatgaggcc    4620
acaggtcatt tacatccaac tgtgaagaga ttgacaagca cactgctgtg attgcttcca    4680
tatatgctgt gtctgcttct gcgaagatag aaaatataaa cagaatgagg agacgaagag    4740
cagattaaaa gtgagcagac aagcagagca aaacccctct gcccttctga aggaaaaaaa    4800
aataacttct taatgtagct tgtctcatat aaggagaata attagatcta tttgctttta    4860
gtgtatttat tctatgagca gggaaagcct ttaaatcctt aagtgctact tagaaaatag    4920
ctttaattct taactgttta ttaagtctgt aagtttaata atgataaagc tataattgac    4980
aaaatccaca tctgtacttc cagtttattg acagctcatt cagcagcccc taaatttctt    5040
gggaagagca ggtgttggag gcagagcagt aaaagattga gatgatctca tcctgtctta    5100
gagctttggc catggaatca gaatcacaga atatcccaag tttggaggga tctgtaagga    5160
tcatcgagtc caattgtgat gtttaaaaca tgtcatttag caatgaggtg ttgaggagaa    5220
gcagtgaagg ccagcagatg gatgtctgtc aggatggtcc ctcctggtca ctgctagtcc    5280
cttcttgttt gaaaggaaac acccaaaatc tccactggtt aaaacttgtc actagaaccc    5340
atctaggaga gtcctgagct tctgctgata agctgtaaaa tcaattgtga tcaaacatga    5400
tcacaagtga gacaattcta gggatgcctg gagggaaatg acccacagag gccaaaatac    5460
aggtatacaa ctggggtttt ctacctaaac tgaggtgctg agagtttgaa caggcaccct    5520
accctataac accctgttgc tcaccatgga tggtgttgca atccttttga attaagcatg    5580
tggctccatg aggctggcac cagtaagcca ggacctccaa atgacagagt acaactgatg    5640
gaatcactga ggtttgaaga cacctctaag accattgagc ccaaccagct catccttgag    5700
ctcctgtggc tgccctcaga gctgctacac cctcatctct gttcattacc aggttgtgat    5760
tatttgggag gaagcttgcc tcctccttcc agccaggaga gccctctcag agcatggaag    5820
caattagtat tttcagtcaa tccaatatat gctgtcagtc tgcaaatagc caactaaaca    5880
acatgccagc gtgctgccat gctgtcagtc tgcaaatagc caactaaaca actagccagc    5940
gtgctgccag tccccttcta cggactgctg gtctcccagg ataacttca ggaaagctgt    6000
ttcatttggg aaagttattc catggcatct gctgcaggac atacagctga gagggagaag    6060
```

```
tcctcccaag cacaggagaa catctcccat cctatggaag caccgaattg tgcaggagat    6120
aaccaactga aaaacacaaa cttacatcct aacccagggg atcatctcca gtagtccaat    6180
ttttgataga caaatgtaag tacaaattta tgtctggtaa aagccaagaa aatgggtcaa    6240
gcaaaattta tccaaagcac attgtctgaa gaatgatgtg atatattcag caaaaccgat    6300
gtcaagaaat tgacagaagt ttaaaataat agcagatgac ttcagagatt ttcagtgatt    6360
tctggaatat attataaaag caaaaatatt tgcactgatc tgtgatattt aaagatgtaa    6420
ctgggaagaa tcactgttca gatgtgttgt tgttacccca gacagaagca ggtagtgagt    6480
ttgtgcacat gtgtggagag tggagaccct ggcaaaaaat ggagatctgg caaaattcaa    6540
agctgggtga gcagcctgct taccctgtgt gttctaaagt gggggctgaa ggcatctcaa    6600
acttactgcc ttctgcaaaa cgagcatgta accccatccc gcaacgtcag gtggcagtat    6660
taaagcactg aaggcttgag tacagtctct attaggcaac ctggttcact aaaagtagg     6720 tggaaatcta ccaccaccaa tgtaggagag caccttgtgt ctcttcatct ggggagtgga    6780
gatacaacta acaatccttc atctagggag ggagacttat gtggggacct gaagcaattt    6840
gagagtacag ctgagaacaa gaaaccatac aaaaggaaaa tatgcatatt ttttagccgt    6900
agaaaatact tggttgtgta tgcatgtgtt attatgacta tatagtgtta ttactatatc    6960
tttaatgata tagtacagtt ctgtatttaa tctgttgccc cacctgcagc tgttaattgc    7020
tcagaaaatg agcctctgtg gtggcaaaat gttgtcttat ttatccgtgt tttaacactg    7080
atatatatct ctggtttgtt ctgatactac aggaagaatg attttatttc cagaatctta    7140
ctgttgctcc aagttctcct ttttttttaa aaatgaaaag tttagtttgg gctatccagt    7200
agcagctgtt ggagcatttg tgctccagca aggagttatg gtgtctggct ttgtgtttct    7260
gttctaggct tgttggtaga gaatggcatt gccagctctg cattttatag catatttcaa    7320
atatttatat ttagcagttt gccccgtttt cattccttgt tacagctcaa ataaaatgag    7380
agcttttact tgtaacccct tttcttccat gaagcttttta ttgacccagc aatctgattt    7440
ctgattattt gcctaattag ttgccttatt aaagctcact cttctttctt ctggaaaaag    7500
taccttctgg aataatgtcg gcccttaaga aaatgatgaa aattactgaa attctcaaga    7560
ttttaactat gagaccatta gagagttggt atttgagtta caacttttgat gtctcagatg    7620 tgaatgtttg gcgtctccat tcttctgcac cttcagtagc aataaaacat taatgtcctg    7680
taaaggttaa ttccttttct ttgagacctt accactgtca aataggttct tccaagacca    7740
cattcctctg tgtctccttg cctgtctgta aggtgataca gtgataacgt gtctggggag    7800
agtttgagtg ccacaactct cccataaaaa gtttcttatt tagaagaaaa aggaaataat    7860
attataggag tggagtaaag ttaaaccagg tgagttgtgc taaaatggca tacttgggaa    7920
gttgtccaag tccaaataaa gagctttatt tttgtgataa ggaaaggatt aaattcttct    7980
catgtctgtc cgttatggat agccaacaat cagaccatgc aactatatgg caaagaagcc    8040
aatggggtaa tactcttctc tgaactgttg gttttttttcc atactggaac cttacagaaa    8100
atgtccctac tcttcattat gtgggcaaaa ctgacaggta gcgatgtgct tgtactgctg    8160
cacttggcgt tgtgctgcta tggaagaatc tcgaaaggct gctctgcatt tgattgaaga    8220
gttagtgtcc aatttcccac agttgtggta tttggaggaa gttttaacag tggtacatag    8280
aggagcaata gatgagtgtc tctctgcctt ggaagaagct t                        8321
```

<210> SEQ ID NO 2
<211> LENGTH: 5027

<212> TYPE: DNA
<213> ORGANISM: Gallus gallus

<400> SEQUENCE: 2

| | | | | | |
|---|---|---|---|---|---|
| ggcacgaagg | gaggcgagag | gatcccggag | cagctggagc | aggcggccgc | gcccgtcctc | 60 |
| ctcttcctgc | agctgccgcc | atggcgccgt | gccgcgctgc | ctgtcgtctg | ccgcttctgg | 120 |
| tagcggtggc | gagcgccggg | ctgggcggct | acttcggcac | caagtcccgc | tacgaggagg | 180 |
| tgaacccgca | cctggcggag | gacccgctgt | ccctcgggcc | gcacgccgcc | gccgccggc | 240 |
| tgcccgccgc | ctgcgccccg | ctgcagctcc | gccgcgtcgt | ccgccacggc | acccgctacc | 300 |
| ccacggccgg | gcaaatccgc | cgcctggccg | agctgcacgg | ccgcctccgc | cgcgccgccg | 360 |
| ccccgtcctg | ccccgccgcc | gccgcgctgg | ccgcctggcc | gatgtggtac | gaggagagcc | 420 |
| tcgacgggcg | gctggcgccg | cggggccgcc | gcgacatgga | acacctggcg | cgccgcctgg | 480 |
| ccgcccgctt | ccccgcgctc | ttcgccgccc | gccgccgcct | ggcgctggcc | agcagctcca | 540 |
| agcaccgctg | cctgcagagc | ggcgcggcct | tccggcgcgg | cctcgggccc | tccctcagcc | 600 |
| tcggcgccga | cgagcggag | atcgaagtga | acgacgcgct | gatgaggttt | tttgatcact | 660 |
| gcgacaagtt | cgtggccttc | gtggaggaca | cgacacagc | catgtaccaa | gtgaacgcct | 720 |
| tcaaagaggg | cccggagatg | aggaaggtgt | tggagaaggt | ggcgagtgcc | ctgtgtctgc | 780 |
| cggccagcga | gctgaacgca | gatctcgttc | aagtggcttt | cctcacttgc | tcgtatgagt | 840 |
| tggctataaa | aaatgtgacc | tccccgtggt | gttcgctctt | cagtgaagaa | gatgctaagg | 900 |
| tactggagta | cctgaatgac | ctgaagcaat | actggaagag | aggatatggc | tatgacatca | 960 |
| atagtcgctc | cagctgcatt | ttattccagg | atatcttcca | gcagttggac | aaagcagtgg | 1020 |
| atgagagcag | aagttgacag | attgaaaata | gaggtagcct | tgcaattttg | gatcagagga | 1080 |
| atgatctatc | aaattgtgaa | gtcttcctcc | ttggaagaaa | agcttcaaaa | gctgccctgg | 1140 |
| cactaccctg | ggatacagcc | tccagaggtc | ccttcccacc | tcaagcattc | tgtaacgcca | 1200 |
| atcacttctt | acaaagagga | ctgcgaagaa | gttgttcatc | tagattttg | ctcactgagg | 1260 |
| atctgagtta | aatatcaaca | gtgatagaac | tgactgttaa | gtcagttgaa | gcagaattct | 1320 |
| cagtcagttg | gcttttttgt | tgtgcttcag | tgctggatgc | agagatgctg | tgtgttaagc | 1380 |
| cctcttcatt | ttgctatgaa | caggctagaa | cttgttgtaa | gctagttgta | agcatgaaac | 1440 |
| caacatagca | ccgaggacta | attgtgaagg | aaaggtgggc | agaaggaagt | ggctgttgat | 1500 |
| agcaaactct | ctgcagcaag | cctggacatt | gtgctgctaa | atcattctgg | tttttggaaa | 1560 |
| tctaagggct | gtcagagctg | ttgatccctc | tcattttgag | agtggtggag | tcaaagctgt | 1620 |
| ggttatgcta | gattgcccctt | taaataaatc | tctactgtat | cctttcttca | gcattctggg | 1680 |
| aagctaaata | aaaatgcat | gaggccacag | gtcatttaca | tccaactgtg | aagagattga | 1740 |
| caagcacact | gctgtgattg | cttccatata | tgctgtgtct | gcttctgcga | agatagaaaa | 1800 |
| tataaacaga | atgaggagac | gaagagcaga | ttaaaagtga | gcagacaagc | agagcaaaac | 1860 |
| ccctctgccc | ttctgaagga | aaaaaaata | acttcttaat | gtagcttgtc | tcatataagg | 1920 |
| agaataatta | gatctatttg | cttttagtgt | atttattcta | tgagcaggga | aagcctttaa | 1980 |
| atccttaagt | gctacttaga | aaatagcttt | aattcttaac | tgtttattaa | gtctgtaagt | 2040 |
| ttaataatga | taaagctata | attgacaaaa | tccacatctg | tacttccagt | ttattgacag | 2100 |
| ctcattcagc | agcccctaaa | tttcttggga | agagcaggtg | ttggaggcag | agcagtaaaa | 2160 |
| gattgagatg | atctcatcct | gtcttagagc | tttggccatg | gaatcagaat | cacagaatat | 2220 |
| cccaagtttg | gagggatctg | taaggatcat | cgagtccaat | tgtgatgttt | aaaacatgtc | 2280 |

```
atttagcaat gaggtgttga ggagaagcag tgaaggccag cagatggatg tctgtcagga    2340
tggtccctcc tggtcactgc tagtcccttc ttgtttgaaa ggaaacaccc aaaatctcca    2400
ctggttaaaa cttgtcacta gaacccatct aggagagtcc tgagcttctg ctgataagct    2460
gtaaaatcaa ttgtgatcaa acatgatcac aagtgagaca attctaggga tgcctggagg    2520
gaaatgaccc acagaggcca aaatacaggt atacaactgg ggttttctac ctaaactgag    2580
gtgctgagag tttgaacagg caccctaccc tataacaccc tgttgctcac catggatggt    2640
gttgcaatcc ttttgaatta agcatgtggc tccatgaggc tggcaccagt aagccaggac    2700
ctccaaatga cagagtacaa ctgatggaat cactgaggtt tgaagacacc tctaagacca    2760
ttgagcccaa ccagctcatc cttgagctcc tgtggctgcc ctcagagctg ctacaccctc    2820
atctctgttc attaccaggt tgtgattatt tgggaggaag cttgcctcct ccttccagcc    2880
aggagagccc tctcagagca tggaagcaat tagtattttc agtcaatcca atatatgctg    2940
tcagtctgca aatagccaac taaacaacat gccagcgtgc tgccatgctg tcagtctgca    3000
aatagccaac taaacaacta gccagcgtgc tgccagtccc cttctacgga ctgctggtct    3060
cccagggata acttcaggaa agctgtttca tttgggaaag ttattccatg gcatctgctg    3120
caggacatac agctgagagg gagaagtcct cccaagcaca ggagaacatc tcccatccta    3180
tggaagcacc gaattgtgca ggagataacc aactgaaaaa cacaaactta catcctaacc    3240 cagggggatca tctccagtag tccaatttttt gatagacaaa tgtaagtaca aatttatgtc    3300
tggtaaaagc caagaaaatg ggtcaagcaa aatttatcca aagcacattg tctgaagaat    3360
gatgtgatat attcagcaaa accgatgtca agaaattgac agaagtttaa ataatagca    3420 gatgacttca gagattttca gtgatttctg gaatatatta taaaagcaaa aatatttgca    3480
ctgatctgtg atatttaaag atgtaactgg gaagaatcac tgttcagatg tgttgttgtt    3540
accccagaca gaagcaggta gtgagtttgt gcacatgtgt ggagagtgga gaccctggca    3600
aaaaatggag atctggcaaa attcaaagct gggtgagcag cctgcttacc ctgtgtgttc    3660
taaagtgggg gctgaaggca tctcaaactt actgccttct gcaaaacgag catgtaaccc    3720
catcccgcaa cgtcaggtgg cagtattaaa gcactgaagg cttgagtaca gtctctatta    3780
ggcaacctgg ttcacttaaa agtaggtgga aatctaccac caccaatgta ggagagcacc    3840
ttgtgtctct tcatctgggg agtggagata caactaacaa tccttcatct agggagggag    3900
acttatgtgg ggacctgaag caatttgaga gtacagctga gaacaagaaa ccatacaaaa    3960
ggaaaatatg catatttttt agccgtagaa aatacttggt tgtgtatgca tgtgttatta    4020
tgactatata gtgttattac tatatctttta atgatatagt acagttctgt atttaatctg    4080
ttgccccacc tgcagctgtt aattgctcag aaaatgagcc tctgtggtgg caaaatgttg    4140
tcttatttat ccgtgtttta acactgatat atatctctgg tttgttctga tactacagga    4200
agaatgattt tatttccaga atcttactgt tgctccaagt tctccttttt ttttaaaaat    4260 gaaagttta gtttgggcta tccagtagca gctgttggag catttgtgct ccagcaagga    4320
gttatggtgt ctggctttgt gtttctgttc taggcttgtt ggtagagaat ggcattgcca    4380
gctctgcatt ttatagcata tttcaaatat ttatatttag cagtttgccc cgttttcatt    4440
ccttgttaca gctcaaataa aatgagagct tttacttgta acccttttttc ttccatgaag    4500 cttttattga cccagcaatc tgatttctga ttatttgcct aattagttgc cttattaaag    4560
ctcactcttc tttcttctgg aaaaagtacc ttctggaata atgtcggccc ttaagaaaat    4620
gatgaaaatt actgaaattc tcaagatttt aactatgaga ccattagaga gttggtattt    4680
```

-continued

```
gagttacaac tttgatgtct cagatgtgaa tgtttggcgt ctccattctt ctgcaccttc    4740
agtagcaata aacattaat gtcctgtaaa ggttaattcc ttttctttga gaccttacca     4800
ctgtcaaata ggttcttcca agaccacatt cctctgtgtc tccttgcctg tctgtaaggt    4860
gatacagtga taacgtgtct ggggagagtt tgagtgccac aactctccca taaaaagttt    4920
cttatttaga agaaaaagga aataatatta taggagtgga gtaaagttaa accaggtgag    4980
ttgtgctaaa atggcatact tgggaagttg tccaagtcca aataaag                  5027
```

<210> SEQ ID NO 3
<211> LENGTH: 318
<212> TYPE: PRT
<213> ORGANISM: Gallus gallus

<400> SEQUENCE: 3

```
Met Ala Pro Cys Arg Ala Ala Cys Leu Leu Pro Leu Leu Val Ala Val
 1               5                  10                  15

Ala Ser Ala Gly Leu Gly Gly Tyr Phe Gly Thr Lys Ser Arg Tyr Glu
            20                  25                  30

Glu Val Asn Pro His Leu Ala Glu Asp Pro Leu Ser Leu Gly Pro His
        35                  40                  45

Ala Ala Ala Ala Arg Leu Pro Ala Ala Cys Ala Pro Leu Gln Leu Arg
    50                  55                  60

Arg Val Val Arg His Gly Thr Arg Tyr Pro Thr Ala Gly Gln Ile Arg
65                  70                  75                  80

Arg Leu Ala Glu Leu His Gly Arg Leu Arg Arg Ala Ala Ala Pro Ser
                85                  90                  95

Cys Pro Ala Ala Ala Leu Ala Ala Trp Pro Met Trp Tyr Glu Glu
            100                 105                 110

Ser Leu Asp Gly Arg Leu Ala Pro Arg Gly Arg Arg Asp Met Glu His
        115                 120                 125

Leu Ala Arg Arg Leu Ala Ala Arg Phe Pro Ala Leu Phe Ala Ala Arg
    130                 135                 140

Arg Arg Leu Ala Leu Ala Ser Ser Ser Lys His Arg Cys Leu Gln Ser
145                 150                 155                 160

Gly Ala Ala Phe Arg Arg Gly Leu Gly Pro Ser Leu Ser Leu Gly Ala
                165                 170                 175

Asp Glu Thr Glu Ile Glu Val Asn Asp Ala Leu Met Arg Phe Phe Asp
            180                 185                 190

His Cys Asp Lys Phe Val Ala Phe Val Glu Asp Asn Asp Thr Ala Met
        195                 200                 205

Tyr Gln Val Asn Ala Phe Lys Glu Gly Pro Glu Met Arg Lys Val Leu
    210                 215                 220

Glu Lys Val Ala Ser Ala Leu Cys Leu Pro Ala Ser Glu Leu Asn Ala
225                 230                 235                 240

Asp Leu Val Gln Val Ala Phe Leu Thr Cys Ser Tyr Glu Leu Ala Ile
                245                 250                 255

Lys Asn Val Thr Ser Pro Trp Cys Ser Leu Phe Ser Glu Glu Asp Ala
            260                 265                 270

Lys Val Leu Glu Tyr Leu Asn Asp Leu Lys Gln Tyr Trp Lys Arg Gly
        275                 280                 285

Tyr Gly Tyr Asp Ile Asn Ser Arg Ser Ser Cys Ile Leu Phe Gln Asp
    290                 295                 300

Ile Phe Gln Gln Leu Asp Lys Ala Val Asp Glu Ser Arg Ser
305                 310                 315
```

<210> SEQ ID NO 4
<211> LENGTH: 2233
<212> TYPE: DNA
<213> ORGANISM: Gallus gallus

<400> SEQUENCE: 4

| | | | | | |
|---|---|---|---|---|---|
| ggcacgaagg | gaggcgagag | gatcccggag | cagctggagc | aggcggccgc | gcccgtcctc | 60 |
| ctcttcctgc | agctgccgcc | atggcgccgt | gccgcgctgc | ctgtcgtctg | ccgcttctgg | 120 |
| tagcggtggc | gagcgccggg | ctgggcggct | acttcggcac | caagtcccgc | tacgaggagg | 180 |
| tgaacccgca | cctggcggag | gacccgctgt | ccctcgggcc | gcacgccgcc | gccgccggc | 240 |
| tgcccgccgc | ctgcgccccg | ctgcagctcc | gccgcgtcgt | ccgccacggc | acccgctacc | 300 |
| ccacggccgg | gcaaatccgc | cgcctggccg | agctgcacgg | ccgcctccgc | cgcgccgccg | 360 |
| ccccgtcctg | ccccgccgcc | gccgcgctgg | ccgcctggcc | gatgtggtac | gaggagagcc | 420 |
| tcgacgggcg | gctggcgccg | cggggccgcc | gcgacatgga | acacctggcg | cgccgcctgg | 480 |
| ccgcccgctt | ccccgcgctc | ttcgccgccc | gccgccgcct | ggcgctggcc | agcagctcca | 540 |
| agcaccgctg | cctgcagagc | ggcgcggcct | tccggcgcgg | cctcgggccc | tccctcagcc | 600 |
| tcggcgccga | cgagcggag | atcgaagtga | acgacgcgct | gatgaggttt | tttgatcact | 660 |
| gcgacaagtt | cgtggccttc | gtggaggaca | cgacacagc | catgtaccaa | gtgaacgcct | 720 |
| tcaaagaggg | cccggagatg | aggaaggtgt | tggagaaggt | ggcgagtgcc | ctgtgtctgc | 780 |
| cggccagcga | gctgaacgca | gatctcgttc | aagtggcttt | cctcacttgc | tcgtatgagt | 840 |
| tggctataaa | aaatgtgacc | tccccgtggt | gttcgctctt | cagtgaagaa | gatgctaagg | 900 |
| tactggagta | cctgaatgac | ctgaagcaat | actggaagag | aggatatggc | tatgacatca | 960 |
| atagtcgctc | cagctgcatt | ttattccagg | atatcttcca | gcagttggac | aaagcagtgg | 1020 |
| atgagagcag | aagttgacag | attgaaaata | gaggtagcct | tgcaattttg | gatcagagga | 1080 |
| atgatctatc | aaattgtgaa | gtcttcctcc | ttggaagaaa | agcttcaaaa | gctgccctgg | 1140 |
| cactaccctg | ggatacagcc | tccagaggtc | ccttcccacc | tcaagcattc | tgtaacgcca | 1200 |
| atcacttctt | acaaagagga | ctgcgaagaa | gttgttcatc | tagattttg | ctcactgagg | 1260 |
| atctgagtta | aatatcaaca | gtgatagaac | tgactgttaa | gtcagttgaa | gcagaattct | 1320 |
| cagtcagttg | gcttttttgt | tgtgcttcag | tgctggatgc | agagatgctg | tgtgttaagc | 1380 |
| cctcttcatt | ttgctatgaa | caggctgaa | cttgttgtaa | gctagttgta | agcatgaaac | 1440 |
| caacatagca | ccgaggacta | attgtgaagg | aaaggtgggc | agaaggaagt | ggctgttgat | 1500 |
| agcaaactct | ctgcagcaag | cctggacatt | gtgctgctaa | atcattctgg | tttttggaaa | 1560 |
| tctaagggct | gtcagagctg | ttgatccctc | tcattttgag | agtggtggag | tcaaagctgt | 1620 |
| ggttatgcta | gattgcccctt | taaataaatc | tctactgtat | cctttcttca | gcattctggg | 1680 |
| aagctaaata | aaaaatgcat | gaggccacag | gtcatttaca | tccaactgtg | aagagattga | 1740 |
| caagcacact | gctgtgattg | cttccatata | tgctgtgtct | gcttctgcga | agatagaaaa | 1800 |
| tataaacaga | atgaggagac | gaagagcaga | ttaaaagtga | gcagacaagc | agagcaaaac | 1860 |
| ccctctgccc | ttctgaagga | aaaaaaaata | acttcttaat | gtagcttgtc | tcatataagg | 1920 |
| agaataatta | gatctatttg | cttttagtgt | atttattcta | tgagcaggga | aagcctttaa | 1980 |
| atccttaagt | gctacttaga | aaatagcttt | aattcttaac | tgtttattaa | gtctgtaagt | 2040 |
| ttaataatga | taaagctata | attgacaaaa | tccacatctg | tacttccagt | ttattgacag | 2100 |
| ctcattcagc | agcccctaaa | tttcttggga | agagcaggtg | ttggaggcag | agcagtaaaa | 2160 |

| gattgagatg atctcatcct gtcttagagc tttggccatg gaatcagaat cacagaatat | 2220 |
| cccaagtttg gag | 2233 |

<210> SEQ ID NO 5
<211> LENGTH: 954
<212> TYPE: DNA
<213> ORGANISM: Gallus gallus

<400> SEQUENCE: 5

| atggcgccgt gccgcgctgc ctgtcgtctg ccgcttctgg tagcggtggc gagcgccggg | 60 |
| ctgggcggct acttcggcac caagtcccgc tacgaggagg tgaacccgca cctggcggag | 120 |
| gacccgctgt ccctcgggcc gcacgccgcc gccgccggc tgcccgccgc ctgcgccccg | 180 |
| ctgcagctcc gccgcgtcgt ccgccacggc acccgctacc ccacggccgg gcaaatccgc | 240 |
| cgcctggccg agctgcacgg ccgcctccgc gcgccgccg ccccgtcctg ccccgccgcc | 300 |
| gccgcgctgg ccgcctggcc gatgtggtac gaggagagcc tcgacgggcg gctggcgccg | 360 |
| cggggccgcc gcgacatgga acacctggcg cgccgcctgg ccgcccgctt ccccgcgctc | 420 |
| ttcgccgccc gccgccgcct ggcgctggcc agcagctcca agcaccgctg cctgcagagc | 480 |
| ggcgcggcct ccggcgcgg cctcgggccc tccctcagcc tcggcgccga cgagacggag | 540 |
| atcgaagtga acgacgcgct gatgaggttt tttgatcact gcgacaagtt cgtggccttc | 600 |
| gtggaggaca cgacacagc catgtaccaa gtgaacgcct tcaaagaggg cccggagatg | 660 |
| aggaaggtgt tggagaaggt ggcgagtgcc ctgtgtctgc cggccagcga gctgaacgca | 720 |
| gatctcgttc aagtggcttt cctcacttgc tcgtatgagt tggctataaa aaatgtgacc | 780 |
| tccccgtggt gttcgctctt cagtgaagaa gatgctaagg tactggagta cctgaatgac | 840 |
| ctgaagcaat actggaagag aggatatggc tatgacatca atagtcgctc cagctgcatt | 900 |
| ttattccagg atatcttcca gcagttggac aaagcagtgg atgagagcag aagt | 954 |

<210> SEQ ID NO 6
<211> LENGTH: 1587
<212> TYPE: DNA
<213> ORGANISM: Gallus gallus

<400> SEQUENCE: 6

| ggcacgaagg gaggcgagag gatcccggag cagctggagc aggcggccgc gcccgtcctc | 60 |
| ctcttcctgc agctgccgcc atggcgccgt gccgcgctgc ctgtcgtctg ccgcttctgg | 120 |
| tagcggtggc gagcgccggg ctgggcggct acttcggcac caagtcccgc tacgaggagg | 180 |
| tgaacccgca cctggcggag gacccgctgt ccctcgggcc gcacgccgcc gccgccggc | 240 |
| tgcccgccgc ctgcgccccg ctgcagctcc gccgcgtcgt ccgccacggc acccgctacc | 300 |
| ccacggccgg gcaaatccgc cgcctggccg agctgcacgg ccgcctccgc gcgccgccg | 360 |
| ccccgtcctg ccccgccgcc gccgcgctgg ccgcctggcc gatgtggtac gaggagagcc | 420 |
| tcgacgggcg gctggcgccg cggggccgcc gcgacatgga acacctggcg cgccgcctgg | 480 |
| ccgcccgctt ccccgcgctc ttcgccgccc gccgccgcct ggcgctggcc agcagctcca | 540 |
| agcaccgctg cctgcagagc ggcgcggcct ccggcgcgg cctcgggccc tccctcagcc | 600 |
| tcggcgccga cgagacggag atcgaagtga acgacgcgct gatgaggttt tttgatcact | 660 |
| gcgacaagtt cgtggccttc gtggaggaca cgacacagc catgtaccaa gtgaacgcct | 720 |
| tcaaagaggg cccggagatg aggaaggtgt tggagaaggt ggcgagtgcc ctgtgtctgc | 780 |
| cggccagcga gctgaacgca gatctcgttc aagtggcttt cctcacttgc tcgtatgagt | 840 |

```
tggctataaa aaatgtgacc tccccgtggt gttcgctctt cagtgaagaa gatgctaagg    900
tactggagta cctgaatgac ctgaagcaat actggaagag aggatatggc tatgacatca    960
atagtcgctc cagctgcatt ttattccagg atatcttcca gcagttggac aaagcagtgg   1020
atgagagcag aagttcaaaa cccatttctt cacctttgat tgtacaagtt ggacatgcag   1080
aaacacttca gccacttctt gctcttatgg gctacttcaa agatgctgag cctctccagg   1140
ccaacaatta catccgccag gcgcatcgga agttccgcag cggccggata gtgccttatg   1200
cagccaacct ggtgtttgtg ctgtaccact gtgagcagaa gacctctaag gaggagtacc   1260
aagtgcagat gttgctgaat gaaaagccaa tgctctttca tcactcgaat gaaaccatct   1320
ccacgtatgc agacctcaag agctattaca aggacatcct tcaaaactgt cacttcgaag   1380
aagtgtgtga attgcccaaa gtcaatggta ccgttgctga cgaactttga gggaatgaaa   1440
tggagtggcc gatttggaaa ccgatctcag ttttcttcaa cagatgttgt gaacgagcac   1500
tttggatgca atgctgctgc tgtgccgact ctctaagctc gcagatttga cggccgttat   1560
ttacctgggt tgtctctgtc agctcaa                                       1587
```

```
<210> SEQ ID NO 7
<211> LENGTH: 449
<212> TYPE: PRT
<213> ORGANISM: Gallus gallus

<400> SEQUENCE: 7
```

```
Met Ala Pro Cys Arg Ala Ala Cys Leu Leu Pro Leu Leu Val Ala Val
 1               5                  10                  15

Ala Ser Ala Gly Leu Gly Gly Tyr Phe Gly Thr Lys Ser Arg Tyr Glu
            20                  25                  30

Glu Val Asn Pro His Leu Ala Glu Asp Pro Leu Ser Leu Gly Pro His
        35                  40                  45

Ala Ala Ala Ala Arg Leu Pro Ala Ala Cys Ala Pro Leu Gln Leu Arg
    50                  55                  60

Arg Val Val Arg His Gly Thr Arg Tyr Pro Thr Ala Gly Gln Ile Arg
65                  70                  75                  80

Arg Leu Ala Glu Leu His Gly Arg Leu Arg Ala Ala Ala Pro Ser
                85                  90                  95

Cys Pro Ala Ala Ala Leu Ala Ala Trp Pro Met Trp Tyr Glu Glu
            100                 105                 110

Ser Leu Asp Gly Arg Leu Ala Pro Arg Gly Arg Asp Met Glu His
        115                 120                 125

Leu Ala Arg Arg Leu Ala Ala Arg Phe Pro Ala Leu Phe Ala Ala Arg
    130                 135                 140

Arg Arg Leu Ala Leu Ala Ser Ser Lys His Arg Cys Leu Gln Ser
145                 150                 155                 160

Gly Ala Ala Phe Arg Arg Gly Leu Gly Pro Ser Leu Ser Leu Gly Ala
                165                 170                 175

Asp Glu Thr Glu Ile Glu Val Asn Asp Ala Leu Met Arg Phe Asp
            180                 185                 190

His Cys Asp Lys Phe Val Ala Phe Val Glu Asp Asn Asp Thr Ala Met
        195                 200                 205

Tyr Gln Val Asn Ala Phe Lys Glu Gly Pro Glu Met Arg Lys Val Leu
    210                 215                 220

Glu Lys Val Ala Ser Ala Leu Cys Leu Pro Ala Ser Glu Leu Asn Ala
225                 230                 235                 240
```

```
Asp Leu Val Gln Val Ala Phe Leu Thr Cys Ser Tyr Glu Leu Ala Ile
                245                 250                 255

Lys Asn Val Thr Ser Pro Trp Cys Ser Leu Phe Ser Glu Glu Asp Ala
                260                 265                 270

Lys Val Leu Glu Tyr Leu Asn Asp Leu Lys Gln Tyr Trp Lys Arg Gly
                275                 280             285

Tyr Gly Tyr Asp Ile Asn Ser Arg Ser Ser Cys Ile Leu Phe Gln Asp
            290                 295                 300

Ile Phe Gln Gln Leu Asp Lys Ala Val Asp Glu Ser Arg Ser Ser Lys
305                 310                 315                 320

Pro Ile Ser Ser Pro Leu Ile Val Gln Val Gly His Ala Glu Thr Leu
                325                 330                 335

Gln Pro Leu Leu Ala Leu Met Gly Tyr Phe Lys Asp Ala Glu Pro Leu
                340                 345                 350

Gln Ala Asn Asn Tyr Ile Arg Gln Ala His Arg Lys Phe Arg Ser Gly
                355                 360                 365

Arg Ile Val Pro Tyr Ala Ala Asn Leu Val Phe Val Leu Tyr His Cys
    370                 375                 380

Glu Gln Lys Thr Ser Lys Glu Glu Tyr Gln Val Gln Met Leu Leu Asn
385                 390                 395                 400

Glu Lys Pro Met Leu Phe His His Ser Asn Glu Thr Ile Ser Thr Tyr
                405                 410                 415

Ala Asp Leu Lys Ser Tyr Tyr Lys Asp Ile Leu Gln Asn Cys His Phe
                420                 425                 430

Glu Glu Val Cys Glu Leu Pro Lys Val Asn Gly Thr Val Ala Asp Glu
                435                 440                 445

Leu
```

<210> SEQ ID NO 8
<211> LENGTH: 1347
<212> TYPE: DNA
<213> ORGANISM: Gallus gallus

<400> SEQUENCE: 8

```
atggcgccgt gccgcgctgc ctgtcgtctg ccgcttctgg tagcggtggc gagcgccggg     60
ctgggcggct acttcggcac caagtcccgc tacgaggagg tgaacccgca cctggcggag    120
gacccgctgt ccctcgggcc gcacgccgcc gccgccggc tgcccgccgc ctgcgccccg    180
ctgcagctcc gccgcgtcgt ccgccacggc accgctacc ccacgccgg gcaaatccgc    240
cgcctggccg agctgcacgg ccgcctccgc cgcgccgccg cccgtcctg cccgccgcc    300
gccgcgctgg ccgcctggcc gatgtggtac gaggagagcc tcgacgggcg gctggcgccg    360
cggggccgcc gcgacatgga cacctggcg cgccgcctgg ccgcccgctt cccgcgcctc    420
ttcgccgccc gccgccgcct ggcgctggcc agcagctcca gcaccgctg cctgcagagc    480
ggcgcggcct tccggcgcgg cctcgggccc tccctcagcc tcggcgccga cgagacggag    540
atcgaagtga cgacgcgct gatgaggttt tttgatcact gcgacaagtt cgtggccttc    600
gtggaggaca cgacacagc catgtaccaa gtgaacgcct tcaaagaggg cccggagatg    660
aggaaggtgt tggagaaggt ggcgagtgcc ctgtgtctgc cggccagcga gctgaacgca    720
gatctcgttc aagtggcttt cctcacttgc tcgtatgagt tggctataaa aaatgtgacc    780
tccccgtggt gttcgctctt cagtgaagaa gatgctaagg tactggagta cctgaatgac    840
ctgaagcaat actggaagag aggatatggc tatgacatca atagtcgctc cagctgcatt    900
ttattccagg atatcttcca gcagttggac aaagcagtgg atgagagcag aagttcaaaa    960
```

```
cccatttctt cacctttgat tgtacaagtt ggacatgcag aaacacttca gccacttctt    1020
gctcttatgg gctacttcaa agatgctgag cctctccagg ccaacaatta catccgccag    1080
gcgcatcgga agttccgcag cggccggata gtgccttatg cagccaacct ggtgtttgtg    1140
ctgtaccact gtgagcagaa gacctctaag gaggagtacc aagtgcagat gttgctgaat    1200
gaaaagccaa tgctctttca tcactcgaat gaaaccatct ccacgtatgc agacctcaag    1260
agctattaca aggacatcct tcaaaactgt cacttcgaag aagtgtgtga attgcccaaa    1320
gtcaatggta ccgttgctga cgaactt                                        1347

<210> SEQ ID NO 9
<211> LENGTH: 446
<212> TYPE: DNA
<213> ORGANISM: Gallus gallus

<400> SEQUENCE: 9
ctgatgaggt tttttgatca ctgcgacaag ttcgtggcct tcgtggagga caacgacaca     60
gccatgtacc aagtgaacgc cttcaaagag ggcccggaga tgaggaaggt gttggagaag    120
gtggcgagtg ccctgtgtct gccggccagc gagctgaacg cagatctcgt tcaagtggct    180
ttcctcactt gctcgtatga gttggctata aaaaatgtga cctccccgtg gtgttcgctc    240
ttcagtgaag aagatgctaa ggtactggag tacctgaatg acctgaagca atactggaag    300
agaggatatg gctatgacat caatagtcgc tccagctgca ttttattcca ggatatcttc    360
cagcagttgg acaaagcagt ggatgagagc agaagttcaa acccatttc ttcacctttg     420 attgtacaag ttggacatgc agaaac                                         446

<210> SEQ ID NO 10
<211> LENGTH: 446
<212> TYPE: DNA
<213> ORGANISM: Homo sapiens

<400> SEQUENCE: 10
ctaatgagat tttttgatca ctgtgagagg ttttaactg aagtagaaaa aaatgctaca      60
gctctttatc acgtggaagc cttcaaaact ggaccagaaa tgcagaacat tttaaaaaaa    120
gttgcagcta ctttgcaagt gccagtaaat gatttaaatg cagatttaat tcaagtagcc    180
tttttcacct gttcatttga cctggcaatt aaaggtgtta atctccttg gtgtgatgtt     240 tttgacatag atgatgcaaa ggtattagaa tatttaaatg atctgaaaca atattggaaa    300
agaggatatg ggtatactat taacagtcga tccagctgca ccttgtttca ggatatcttt    360
cagcacttgg acaaagcagt tgaacagaaa caaaggtctc agccaatttc ttctccagtc    420
atcctccagt ttggtcatgc agagac                                         446

<210> SEQ ID NO 11
<211> LENGTH: 151
<212> TYPE: PRT
<213> ORGANISM: Gallus gallus

<400> SEQUENCE: 11

Asp Ala Leu Met Arg Phe Phe Asp His Cys Asp Lys Phe Val Ala Phe
 1               5                  10                  15

Val Glu Asp Asn Asp Thr Ala Met Tyr Gln Val Asn Ala Phe Lys Glu
                20                  25                  30

Gly Pro Glu Met Arg Lys Val Leu Glu Lys Val Ala Ser Ala Leu Cys
            35                  40                  45
```

```
Leu Pro Ala Ser Glu Leu Asn Ala Asp Leu Val Gln Val Ala Phe Leu
         50                  55                  60

Thr Cys Ser Tyr Glu Leu Ala Ile Lys Asn Val Thr Ser Pro Trp Cys
 65                  70                  75                  80

Ser Leu Phe Ser Glu Asp Ala Lys Val Leu Glu Tyr Leu Asn Asp
                 85                  90                  95

Leu Lys Gln Tyr Trp Lys Arg Gly Tyr Gly Tyr Asp Ile Asn Ser Arg
                100                 105                 110

Ser Ser Cys Ile Leu Phe Gln Asp Ile Phe Gln Gln Leu Asp Lys Ala
                115                 120                 125

Val Asp Glu Ser Arg Ser Ser Lys Pro Ile Ser Ser Pro Leu Ile Val
            130                 135                 140

Gln Val Gly His Ala Glu Thr
145                 150

<210> SEQ ID NO 12
<211> LENGTH: 151
<212> TYPE: PRT
<213> ORGANISM: Homo sapiens

<400> SEQUENCE: 12

Asp Lys Leu Met Arg Phe Phe Asp His Cys Glu Xaa Phe Leu Thr Glu
  1               5                  10                  15

Val Glu Lys Asn Ala Thr Ala Leu Tyr His Val Glu Ala Phe Lys Thr
                 20                  25                  30

Gly Pro Glu Met Gln Asn Ile Leu Lys Lys Val Ala Ala Thr Leu Gln
             35                  40                  45

Val Pro Val Asn Asp Leu Asn Ala Asp Leu Ile Gln Val Ala Phe Phe
         50                  55                  60

Thr Cys Ser Phe Asp Leu Ala Ile Lys Gly Val Lys Ser Pro Trp Cys
 65                  70                  75                  80

Asp Val Phe Asp Ile Asp Asp Ala Lys Val Leu Glu Tyr Leu Asn Asp
                 85                  90                  95

Leu Lys Gln Tyr Trp Lys Arg Gly Tyr Gly Tyr Thr Ile Asn Ser Arg
                100                 105                 110

Ser Ser Cys Thr Leu Phe Gln Asp Ile Phe Gln His Leu Asp Lys Ala
                115                 120                 125

Val Glu Gln Lys Gln Arg Ser Gln Pro Ile Ser Ser Pro Val Ile Leu
            130                 135                 140

Gln Phe Gly His Ala Glu Thr
145                 150

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence:  C-terminal
      of longer protein

<400> SEQUENCE: 13

Ala Asp Glu Leu
  1

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence:  C-terminal
``` of luminal proteins in vertebrates

<400> SEQUENCE: 14

Xaa Asp Glu Leu
 1

<210> SEQ ID NO 15
<211> LENGTH: 13
<212> TYPE: DNA
<213> ORGANISM: Artificial Sequence
<220> FEATURE:
<223> OTHER INFORMATION: Description of Artificial Sequence: 3' end
      primer

<400> SEQUENCE: 15 ttttttttttt tca                                                     13

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: primer for
      reamplification

<400> SEQUENCE: 16
ccgcggatcc ttttttttttt tca                                          23

<210> SEQ ID NO 17
<211> LENGTH: 10
<212> TYPE: DNA
<213> ORGANISM: Artificial Sequence
<220> FEATURE:
<223> OTHER INFORMATION: Description of Artificial Sequence: 5' end
      primer

<400> SEQUENCE: 17
cttgattgcc                                                          10

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: primer for
      reamplification

<400> SEQUENCE: 18
ccgcgaattc cttgattgcc                                               20